United States Patent
Jeevanandam et al.

(10) Patent No.: US 8,608,637 B2
(45) Date of Patent: Dec. 17, 2013

(54) INTERNAL DRIVE LINE FOR VENTRICULAR ASSIST DEVICE

(75) Inventors: Valluvan Jeevanandam, Chicago, IL (US); Roger William Snyder, New Braunfels, TX (US); Robert Smith, Raleigh, NC (US); Paul DeDecker, Clinton Township, MI (US)

(73) Assignee: NuPulse, Inc., Tucson, AZ (US)

( * ) Notice: Subject to any disclaimer, the term of this patent is extended or adjusted under 35 U.S.C. 154(b) by 0 days.

(21) Appl. No.: 13/349,087

(22) Filed: Jan. 12, 2012

(65) Prior Publication Data

US 2012/0108886 A1    May 3, 2012

Related U.S. Application Data

(62) Division of application No. 13/300,501, filed on Nov. 18, 2011, now Pat. No. 8,323,174, which is a division of application No. 12/910,467, filed on Oct. 22, 2010, now Pat. No. 8,066,628.

(51) Int. Cl.
    *A61M 1/10* (2006.01)

(52) U.S. Cl.
    USPC .................. 600/17; 600/18; 600/37; 607/119

(58) Field of Classification Search
    USPC ........................... 607/16, 119; 600/17, 18, 37
    See application file for complete search history.

(56) References Cited

U.S. PATENT DOCUMENTS

| | | | |
|---|---|---|---|
| 3,585,983 A | 6/1971 | Kantrowitz et al. | |
| 3,692,018 A | 9/1972 | Goetz et al. | |
| 3,720,199 A * | 3/1973 | Rishton et al. | 600/18 |
| 4,051,840 A | 10/1977 | Kantrowitz et al. | |
| 4,185,617 A | 1/1980 | Hutchins | |
| 4,527,549 A | 7/1985 | Gabbay | |
| 4,540,404 A | 9/1985 | Wolvek | |
| 4,634,430 A * | 1/1987 | Polaschegg | 604/141 |
| 4,785,795 A * | 11/1988 | Singh | 600/18 |
| 4,902,272 A | 2/1990 | Milder et al. | |
| 5,052,934 A | 10/1991 | Carey et al. | |
| 5,147,318 A | 9/1992 | Hohn | |
| 5,509,902 A | 4/1996 | Raulerson | |
| 5,820,542 A | 10/1998 | Dobak, III et al. | |
| 5,833,655 A | 11/1998 | Freed et al. | |
| 5,876,367 A | 3/1999 | Kaganov et al. | |
| 6,030,336 A | 2/2000 | Franchi | |
| 6,132,363 A | 10/2000 | Freed et al. | |
| 6,210,318 B1 | 4/2001 | Lederman | |
| 6,245,008 B1 | 6/2001 | Leschinsky et al. | |
| 6,406,422 B1 | 6/2002 | Landesberg | |

(Continued)

FOREIGN PATENT DOCUMENTS

| | | |
|---|---|---|
| JP | 2002-518106 A | 6/2002 |
| JP | 2005-000434 A | 1/2005 |

OTHER PUBLICATIONS

Bard Dynaflow Instructions for Use (Dec. 2007).

(Continued)

*Primary Examiner* — Michael Kahelin
*Assistant Examiner* — Alyssa M Alter
(74) *Attorney, Agent, or Firm* — Dale F. Regelman; Quarles & Brady LLP

(57) ABSTRACT

Devices and methods are disclosed for implanting, positioning, removing, replacing and operating intra-aortic balloon pumps.

13 Claims, 15 Drawing Sheets

(56) References Cited

U.S. PATENT DOCUMENTS

| | | |
|---|---|---|
| 6,468,200 B1 | 10/2002 | Fischi |
| 6,945,926 B2 | 9/2005 | Trumble |
| 6,961,448 B2 | 11/2005 | Nichols et al. |
| 7,059,338 B1 | 6/2006 | Kincaid et al. |
| 7,374,531 B1 | 5/2008 | Kantrowitz |
| 7,468,050 B1 | 12/2008 | Kantrowitz |
| 7,494,459 B2 | 2/2009 | Anstadt et al. |
| 7,520,850 B2 | 4/2009 | Brockway |
| 7,574,262 B2 | 8/2009 | Haugland et al. |
| 7,892,162 B1 | 2/2011 | Jeevanandam et al. |
| 8,066,628 B1 | 11/2011 | Jeevanandam et al. |
| 2003/0083539 A1 | 5/2003 | Leschinsky |
| 2005/0014991 A1 | 1/2005 | Sugiura |
| 2005/0192604 A1 | 9/2005 | Carson et al. |
| 2006/0063965 A1 | 3/2006 | Aboul-Hosn et al. |
| 2009/0131741 A1 | 5/2009 | Kantrowitz |

OTHER PUBLICATIONS

International Search Report and Written Opinion for PCT/2010/053779 dated Jul. 7, 2011.

Chen, Z., R. Ward, Y. Tian, F. Malizia, D. H. Gracias, Y. R. Shen, and G. A. Somorjai. Interaction of fibrinogen with surfaces of end-group-modified polyurethanes: a surface-specific sum-frequency-generation vibrational spectroscopy study. J. Biomed. Mater. Res., 62 (2002):254-264.

* cited by examiner

INTERNAL DRIVE LINE FOR VENTRICULAR ASSIST DEVICE

CROSS-REFERENCE TO RELATED APPLICATION

This application is a division of U.S. application Ser. No. 13/300,501, filed Nov. 18, 2011, which is a division of U.S. application Ser. No. 12/910,467, filed Oct. 22, 2010, now U.S. Pat. No. 8,066,628, which is hereby incorporated herein by reference.

SUMMARY

Devices and methods are disclosed for implanting, positioning, removing, replacing and operating intra-aortic balloon pumps.

BACKGROUND

The use of intraaortic balloon pumps is a well known method for treating heart failure. The balloon pump is positioned inside the aorta, typically in the proximal descending aorta. The balloon pump (typically 40-50 milliliters in capacity) is inflated and deflated in time with the contraction of the left ventricle. During diastole, the balloon is inflated, thereby driving blood in the ascending aorta and aortic arch into the coronary arteries to supply oxygen to the heart muscle. During systole, as the left ventricle contracts, the balloon is deflated so as to decrease the afterload. This procedure is termed "counterpulsation."

Such balloon pumps also typically require burdensome external equipment to operate, such as gas compressors, gas tanks, and/or condensors.

DETAILED DESCRIPTION

Figure 1:
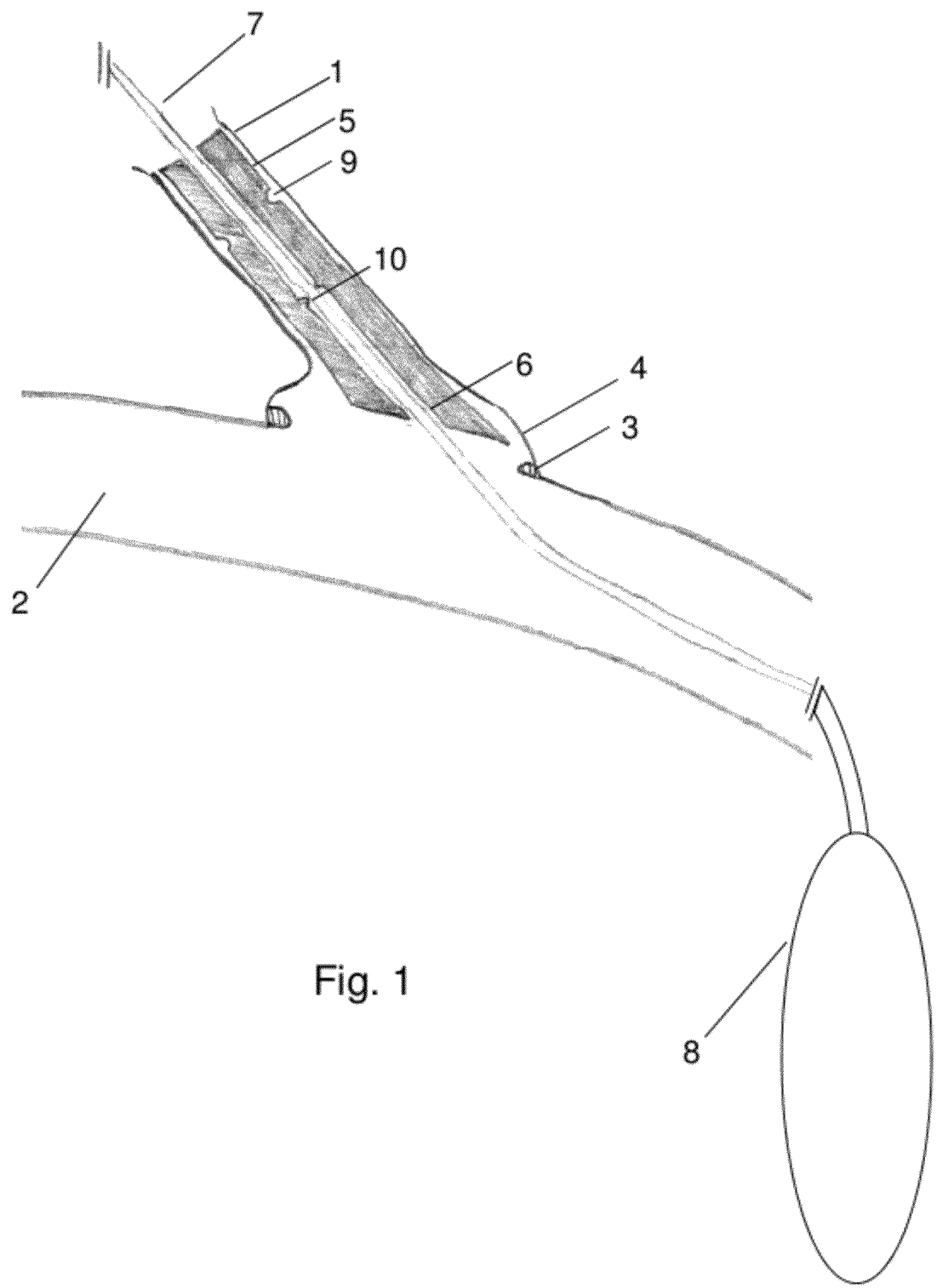
FIG. 1 schematically shows an intraaortic balloon pump implanted in a patient using an arterial interface.

Existing ventricular assist devices and intraaortic balloon pumps suffer from the problem of using inconvenient external apparatuses. Many intraaortic balloon pump systems use helium as a pumping medium, which requires that the patient connect to a cumbersome helium tank. Helium is chosen largely for its extremely low viscosity, allowing the use of a relatively thin drive line between the balloon pump and an external driver. (According to Poiseuille's law, the pressure drop along a fluid line is proportional to the fluid viscosity and inversely proportional to the fourth power of the diameter. A sufficiently low-viscosity fluid can therefore reduce the pressure drop to acceptable levels along even a thin line.) The thin internal drive line is in turn required to avoid occluding the artery through which the drive line is threaded.

Rather than resort to using low-viscosity helium and the attendant helium tank, the inventors have taken a different approach by minimizing the length of the portion of the drive line that must be especially thin. Some parts of the drive line may pass through the thoracic and/or abdominal cavities; there is no reason to keep this section of the line especially thin. Likewise, the portion of the drive line actually dangling in the aorta need not be particularly thin since the aorta is large and is in relatively little danger of being occluded by the drive line. The inventors realized that a small diameter is of greatest benefit in the part of the drive line deployed in a lesser artery, such as the right or left subclavian arteries, the common carotid arteries, or the brachiocephalic (innominate) artery. By keeping the drive line relatively wide in most of its length and narrow only where absolutely necessary, ordinary air can be used as the pumping medium, eliminating the need for a helium tank. Some devices and methods disclosed herein result from this insight.

Existing intraaortic balloon pumps can also be cumbersome because many require removal of humidity from the pumping medium. In essentially any system that causes a pumping medium to interact with blood through anything less than a perfectly water-impermeable material, moisture will gradually seep through the balloon pump and/or drive lines, contaminating the pumping medium with water vapor. Humidity in the pumping medium can change the fluid mechanics of pumping and also increase the risk of microbial contamination. Where the pumping medium is helium, the medium must be conserved while the water is removed, hence the need for a compressor.

Because the inventors have eliminated the need for helium, a far simpler solution is possible, namely external venting of the pumping medium. Using air instead of helium as a pumping medium means that there is always an infinite supply of pumping medium on hand. When the air in the pump has become too moist, one can simply purge the air from the device and fill the device with relatively dry ambient air. In some embodiments described below, an external driver can continuously shift from operating the pump in a closed mode, in which the system is sealed so that no air enters or leaves the system, to an open mode, in which the system can operate without interruption while replacing the air already in the system with fresh external air. The air in the system can be replaced at regular intervals, or only when triggered, for instance by a humidity sensor.

A much more portable system results from eliminating the need for both a helium tank and compressor.

A system that can operate in a closed mode as described above has the added benefit of leak detection. Because no air should be entering or leaving the system in closed mode, the pressure in the system should be the same at identical points in the pumping cycle. If the pressure at a given point in the cycle is dropping over time, one can be confident that there is an air leak somewhere in the system, information that is important to communicate to the patient or a physician.

The inflation/deflation cycles can be triggered based on QRS complex detection from electrocardiogram (EKG) data, by dicrotic notch detection from pressure data, or by both. Electrodes and pressure sensors can be provided as necessary. The balloon itself may function as a pressure sensor, especially in a partially deflated state. Deflation will typically be triggered based on the detection of a QRS complex, which indicates impending systole, while inflation will typically be triggered based on the detection of a dicrotic notch, which indicates the beginning of diastole. Both inflation and deflation events can be triggered by one set of data; for example, inflation may be triggered at a certain predetermined amount of time after QRS detection.

Another problem in using existing intraaortic balloon pumps as long-term devices is that parts can wear out, cause infections, or otherwise need to be replaced. After the graft is attached at the incision in the artery and thereby exposed to the bloodstream, the healing process causes clotted blood, granulation tissue and other material to accumulate around the incision and in the graft. Such tissue completely fills the available volume inside the graft except for the space occupied by the inflation catheter. Such tissue becomes a cohesive, sometimes solid, mass with the graft. Because the balloon, even in its deflated state, is much larger than the inflation catheter (the catheter being small to avoid occupying too much cross-section of the vasculature through which it runs), it is practically impossible to remove the balloon through the clogged graft or to thread a new balloon through. The current solution to this problem is to replace the entire graft every time the balloon is replaced, which requires repeating the highly invasive vascular grafting procedure from the beginning.

The focus, then, has been on avoiding failures that necessitate the costly and dangerous replacement surgeries. For example, extreme care is taken to avoid introducing infections, despite inconvenience and discomfort to the patient. Also, the pumps are made of especially durable materials that are resistant to normal body stresses, even at the expense of more desirable functional characteristics.

But the inventors realized that failures are inevitable; practically no implantable device can forever survive the stresses placed upon it by the living body. Living tissue is constantly repaired and maintained by normal body processes, while implanted devices tend to be attacked, compartmentalized, or otherwise isolated. At the very least, they do not benefit from normal repair and maintenance processes to help them resist normal stresses.

So the inventors hit upon an entirely new strategy: rather than continue dogged efforts at finding ways to prevent failures, they accepted that failures cannot be avoided and instead sought ways to make the replacement procedure faster, simpler, and safer. Some disclosed systems and methods for interfacing the intraaortic balloon pump with the vasculature resulted from this strategy.

The vascular interface incorporates a "stopper" to fill the space between the graft and the inflation catheter. Because this space is filled from the beginning, body processes cannot invade the graft to fill that space with clotted blood, etc. (although there may be some minimal invasion around the stopper itself). As a result, when the time to replace the pump inevitably comes, the stopper can be slipped out of the graft, leaving a largely patent graft lumen. The graft lumen is wide enough to permit removal and replacement of the pump. The graft itself need not be removed and replaced, so the dangerous and time-consuming step of vascular surgery is avoided.

FIG. 1 schematically shows an example of such a device, as deployed in a patient's vasculature. A vascular graft 1 is attached to an artery 2 with a suture ring 3 at the position of an incision in the artery. The particular graft shown flares at its distal end 4. The stopper 5 sits inside the graft 1, filling the interior of the graft 1 except for a hole 6 along the length of the stopper 5. The hole 6 necessarily runs the entire length of the stopper 5, but the stopper 5 need not run the entire length of the graft 1. It is sufficient that some part of the stopper 5 is near the distal end of the graft 4 when properly positioned. In some cases, the stopper can extend out past the proximal end of the graft, to help minimize clot invasion. The stopper can be secured to and immobilized with respect to the graft.

The hole 6 through the length of the stopper 5 is filled by the inflation catheter 7. The inflation catheter 7 in turn is connected at its distal end to a balloon or inflatable chamber 8. A typical inflation catheter will have a diameter in the range 3 to 6 mm (often about 5 mm), although other diameters are possible as well. In preferred embodiments, the catheter will be (i) wide enough inside to lower resistance to fluid flow to the point that air can be used as the pressure medium, with a pressure source that need generate no more than 0.5 atmospheres in order to transmit pressure from the source to the balloon chamber, and (ii) narrow enough outside so that the presence of the inflation catheter in the various blood vessels does not significantly interfere with the flow of blood through the vessels. In this context, "narrow enough to avoid significant interference" means that the catheter occludes less than 50% of the vessel's lumen.

Each component may be constructed of any of a variety of well-known biocompatible materials, such as polytetrafluoroethylene (PTFE), expanded PTFE (ePTFE), polyurethane, polyethylene, polyethylene terephthalate, silicone, and titanium. The inflation catheter 7 and/or balloon 8 in particular may also beneficially comprise a moisture resistant material to help prevent water from blood passing through the balloon wall and building up in the chamber. For example, moisture resistance may be achieved by laminating a moisture resistant material onto or into the inflation catheter 7 and/or balloon 8, or by applying moisture-resistant coating to the inner or outer surface of the balloon wall.

The stopper 5 may be useful in other ways besides preventing the build-up of tissue inside the graft 1. The stopper 5 can act as a cushion surrounding the inflation catheter 7 so as to help maintain the inflation catheter's patency when the graft is tied down. Also, the increased surface area of the stopper 5 as compared to the inflation catheter 7 can ease the task of sealing the graft 1.

Not shown in FIG. 1 is the proximal end of the inflation catheter 7. Because the balloon 8 needs to inflate and deflate in order to function as a ventricular assist device, the balloon pump must be in fluid communication with some sort of driver (e.g. an air compressor or pump) via the inflation catheter. If such a driver is to reside outside the body (as is typically done), a skin interface may be implanted. The skin interface, among other things, can help to decouple the internal parts of the pump assembly from the external parts. The inflation catheter can be attached to the interface, and the interface attached to the fluid driver. In this way, the driver, the inflation catheter 7 and the balloon 8 may form a closed air system; a closed system may include a well-defined and precisely-controlled volume of air, which facilitates leak detection. Air volume and movement of air may be precisely controlled using, for example, a bellows driven by one or more linear actuators. (In discussions of the skin interface and driver herein, the inflation catheter is alternatively referred to as an internal drive line.)

The arterial interface device of FIG. 1 can be implanted in the body in a manner similar to the traditional intraaortic balloon pump described above. The graft 1 is attached to an artery 2 at an incision as described above. In addition to threading the balloon 8 and inflation catheter 7 through the graft 1, the stopper 5 is positioned in the graft 1, surrounding the inflation catheter 7. The balloon 8 is positioned in the descending aorta and, if the stopper 5 is a separate piece from the inflation catheter 7, the stopper 5 is positioned along the inflation catheter 7 so as to fill the distal end of the graft 1, near where the graft 1 is attached to the artery 2. The stopper 5 can be secured to the inflation catheter 7, and graft 1 is secured to the stopper 5.

To remove the balloon 8, one simply detaches the stopper 5 from the graft 1. Because the stopper 5 has prevented clots and other healing tissues from accumulating inside the graft 1, the stopper 5 can be removed easily, leaving the graft 1 unblocked. The balloon pump can then be removed by pulling the inflation catheter 7 and balloon 8 through the graft 1 lumen. A new balloon pump can be advanced through the open graft 1 lumen along with a new stopper 5. In this way, the balloon pump can be replaced without having to remove and replace the graft 1. Because the vascular graft 1 is left intact and relatively undisturbed, no open surgery is necessary to replace a damaged or worn out part. Such a procedure is relatively non-invasive and can be carried out in a catheterization laboratory rather than an operating room.

Figure 2:
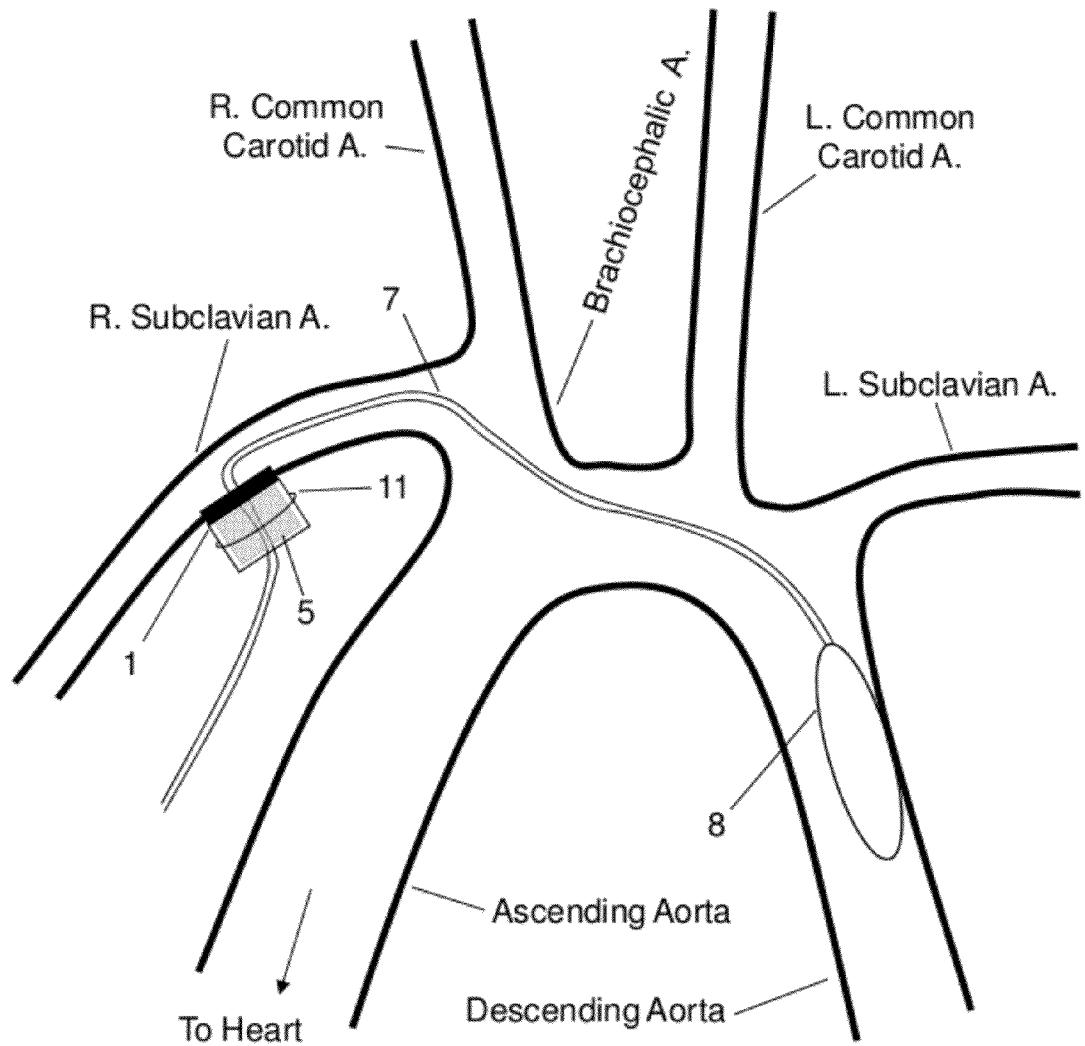
FIG. 2 schematically shows an intraaortic balloon pump positioned in the proximal descending aorta, with the pump's inflation catheter entering the vasculature at the right subclavian artery through an arterial interface.

One of skill in the art will appreciate that many configurations of the stopper 5 are possible. The stopper 5 could be sized to completely fill the graft 1 surrounding the inflation catheter 7, fitting snugly within the graft 1, or the stopper 5 could be smaller than the interior of the graft 1 so that, for example, the graft 1 is cinched down onto the stopper 5 with a suture or tie. (Suture or tie 11 is shown in FIG. 2). The stopper 5 could be integrally formed with the inflation catheter 7. The stopper 5 could have constant cross-sectional geometry, e.g., as a cylinder or prism, or the stopper 5 could be tapered or flared. The stopper 5 could be shaped to fit the interior of the particular vascular graft 1 being used. The stopper 5 could be made of two distinct pieces that form the entire stopper 5 when clamped together around the inflation catheter 7, or the stopper 5 could be a single integral piece with a solid cross-section except for the hole 6 through which the inflation catheter 7 passes. The stopper 5 could be shaped with a circumferential notch 9 around its exterior to provide a convenient groove in which to run a tie or suture when securing the graft 1 to the stopper 5. The stopper 5 could also include a circumferential ridge 10 around the interior surface that defines the hole 6, the ridge 10 acting as a seal between the stopper 5 and the inflation catheter 7.

The hole 6 in the stopper 5 should be large enough to accommodate the inflation catheter 7, but too narrow to pass the balloon 8. Some outer dimension of the stopper 5 should be almost as large as, as large as, or larger than an outer dimension of the balloon 8 so that the balloon 8 can pass through the opening left after the stopper 5 has been removed without undue squeezing or compression. When in place, the stopper 5 should substantially fill the graft apart from the hole 6 for the inflation catheter 7. The hole 6 can account for various fractions of the smallest cross-sectional area of the stopper 5 including 75%, 60%, one half, one third, one quarter, or less.

FIG. 2 shows (schematically) the vascular interface is positioned on the right subclavian artery. This position is advantageous because it allows easy surgical access and a relatively short distance to the descending aorta. FIG. 2 also shows the graft secured to the stopper by a suture 11. Other suitable positions for the interface include either common carotid artery, the brachiocephalic artery, the left subclavian artery, the descending aorta, and the abdominal aorta. Downstream branches of the aorta may also be used, such as the external iliac and femoral arteries.

In addition to the components shown in FIGS. 1 and 2, it may be beneficial for the device to include various sensors. Sensors located at or near the balloon chamber will typically be connected to an electrical wire that, like the inflation catheter, passes through the stopper 5 and graft 1. The wire serves to pass the collected data out of the body, for instance to the fluid driver or an associated processor. Sensors that wirelessly transmit collected data are possible as well. Examples of sensors are electrical leads to measure the electrocardiogram, and sensors that detect pressure directly or indirectly. A wide variety of direct pressure sensors are known; the chamber itself can act as a pressure sensor when partially inflated. Indirect sensors include, for example, a microphone to monitor heart sounds. Data from these sensors can be used to monitor the cardiac cycle and, thereby, the counterpulsation cycle.

Sensors can also be used to determine the state of the air inside the system. Air pressure sensors can be used to detect whether the balloon pump is properly inflating, or if there is a leak in the system. A humidity sensor could be used to detect whether moisture has built up inside the balloon pump. The humidity sensor may be linked to a de-humidifier (such as an active dehumidifier or a vent system to exchange the pumping air with ambient air, described later) so that a certain level of humidity is not exceeded inside the balloon pump.

Sensors for arterial blood pressure may also be included, for example, at the pump or at the stopper. The sensors would communicate the detected arterial blood pressure by a signal the skin interface, either by wire or wirelessly. An arterial blood pressure monitor may similarly be located on the pump.

Although the drawings are directed to an intraaortic balloon pump, other indwelling arterial devices may be positioned using the disclosed arterial interface, such as indwelling arterial catheters ("A-lines"), dialysis lines, blood pumps such as axial flow pumps which add energy to flowing blood, and blood circulators such as those that remove blood from the aorta during systole and return it during diastole. While devices having distal ends larger than the catheters from which they extend may especially benefit, any device that may require replacement may benefit, as the stopper provides a convenient way to restore patency of the vascular graft for insertion of the replacement device.

Figure 3:
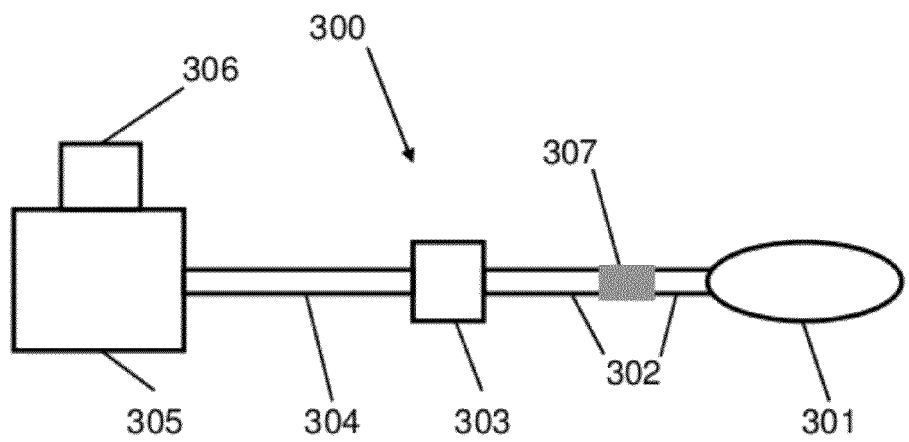
FIG. 3 schematically shows a ventricular assist device including an intra-aortic balloon pump, an internal drive line, a skin interface, an external drive line, and an external driver.

As described above, another improvement in ventricular assist devices is the improvement in portability achieved by eliminating the need for both a helium tank to supply pumping medium, and a compressor to dry the pumping medium. To this end, a ventricular assist device can include an intra-aortic balloon pump, an internal drive line, an arterial interface, a skin interface, an external drive line, an external driver, and a controller. One embodiment of such a ventricular assist device 300 is depicted schematically in FIG. 3.

The intra-aortic balloon pump 301 may be sized and shaped to dangle inside a patient's aorta. The wall of the balloon pump may include moisture resistant material, or may be entirely moisture resistant, to keep the air inside the balloon pump as dry as possible. One possible moisture resistant material for the balloon pump is polyurethane. The polyurethane polymers may be modified to include surface silicone end groups.

At its proximal end, the balloon pump 301 is connected to the distal end of the internal drive line 302. The skin interface 303 connects the proximal end of the internal drive line 302 to the distal end of the external drive line 304. The proximal end of the external drive line 304 is connected to the driver 305. The driver is connected to a controller 306. An arterial interface 307 is sized and shaped to pass the internal drive line 302 through an arterial wall.

The balloon pump 301, the internal drive line 302, the skin interface 303, the external drive line 304, and the driver 305 can be charged with a pumping medium; a preferred pumping medium is air, but any fluid could be used. The balloon pump 301, the internal drive line 302, the skin interface 303, the external drive line 304, and the driver 305 can form a closed fluid system, or can be open, for example if the pumping medium is ambient air. In some embodiments, the balloon pump 301, the internal drive line 302, the skin interface 303, the external drive line 304, and the driver 305 can form a closed fluid system, or may operate in either a closed or open mode. The balloon pump 301 may have various sizes depending on the anatomy of the patient, but will typically have an inflated volume of about 40 to 60 cubic centimeters when inflated to 10 to 20 mmHg above the surrounding pressure.

Figure 4:
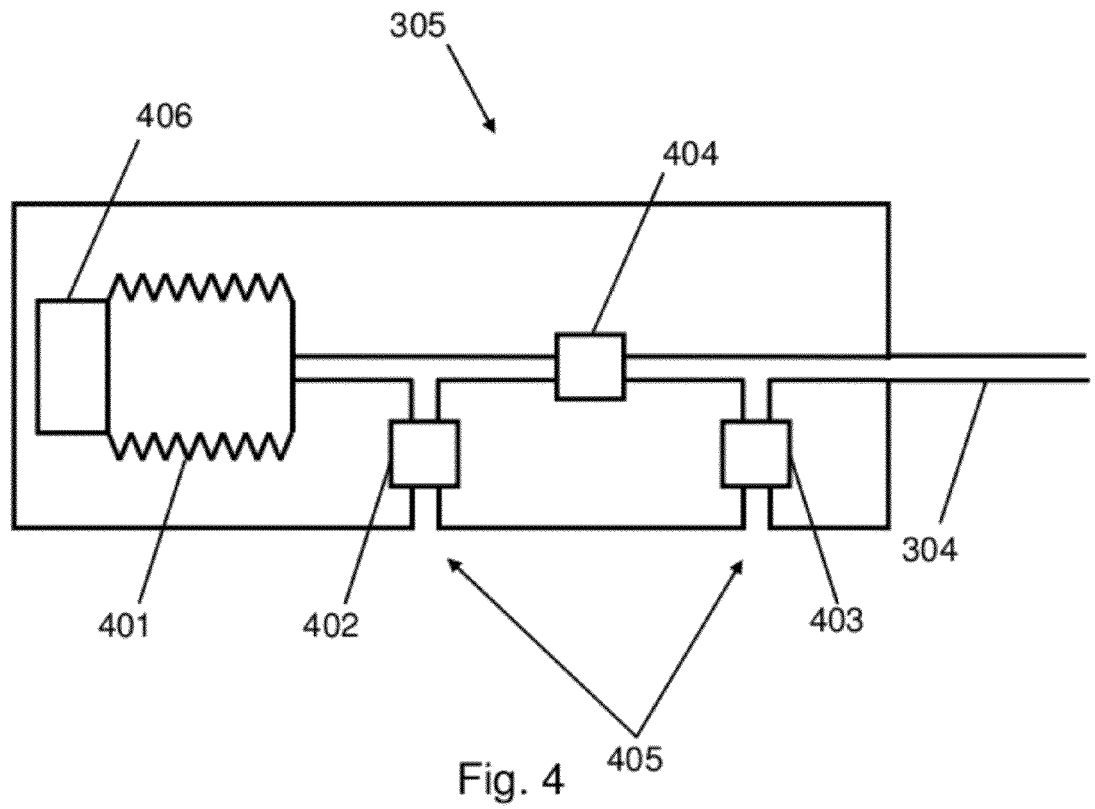
FIG. 4 schematically shows a driver for a ventricular assist device including a bellows and multiple valves.

FIG. 4 schematically depicts one embodiment of the driver 305. The external driver includes a bellows 401 which may be rigid. The bellows 401 are in fluid communication with valves, 402, 403, 404 which are in turn connected to the external drive line 304. The valves 402, 403, 404 can be controlled by the controller 306. Bellows valve 402 is connected at one end to the bellows 401 and at the other end to ambient air 405. Ambient air valve 403 is similarly connected on one end to the external drive line 304, and at the other end to ambient air 405. Pump valve 404 connects the bellows directly to the external drive line 304, and eventually to the pump (not shown in FIG. 4). The amount of air expelled from the bellows 401 determines the pressure increase in the pump 301 during inflation. The bellows 401 are controlled to cause an increase in pressure in the pump 301 by a predetermined amount over the local aortic arterial blood pressure during diastole. The increase over local blood pressure could be in the range of 0 to 50 mmHg, for example 40 mmHg, but not exceeding a predetermined amount. The bellows 401 may have constant cross-sectional geometry along its length so that the volume is varied only by changing the length of the bellows 401.

In a closed configuration, bellows valve 402 and ambient air valve 403 are left closed while pump valve 404 is left open. In this way, the balloon pump 301, the internal drive line 302, the skin interface 303, the external drive line 304, and the driver 305 form a closed fluid system. When bellows 401 contract, they pump air into the external drive line 304 and eventually into the balloon pump; when bellows 401 expand, air is drawn out of the balloon pump through the drive lines 302, 304 and back into the driver 305. In this closed mode, no air is added to or vented from the device.

In an open configuration, ambient air 405 can be drawn into the system through one or both of valves 402 and 403. The ambient air can be used to replace air already in the system, for example if the air in the system has become undesirably moist. Or ambient air 405 can be added to the air already in the system, for example if there is a leak in the system. Or ambient air can be used for the entire pumping cycle. Ambient air 405 can be drawn into the bellows 401 by opening bellows valve 402, closing pump valve 404, and then expanding the bellows 401 from a collapsed state. That same ambient air can then be forced into the external drive line 304 and thence into the pump 301 by closing bellows valve 402 and ambient air valve 403, opening pump valve 404 and collapsing bellows 401. Air can be vented or exhausted from the system by closing pump valve 404 and opening ambient air valve 403 when pump 301 is inflated to above the local blood pressure around pump 301. In some embodiments, the system may have no pump valve and/or only one valve that can open to ambient air.

The bellows 401 can be actuated by a prime mover 405 controlled by the controller 306. The prime mover can be any mover capable of contracting and expanding the bellows 401. In one embodiment, the mover 405 is a screw turned by a motor; the motor rotates one way to advance the screw and compress the bellows 401, and rotates the other way to cause the screw to retreat, expanding the bellows.

Figure 5:
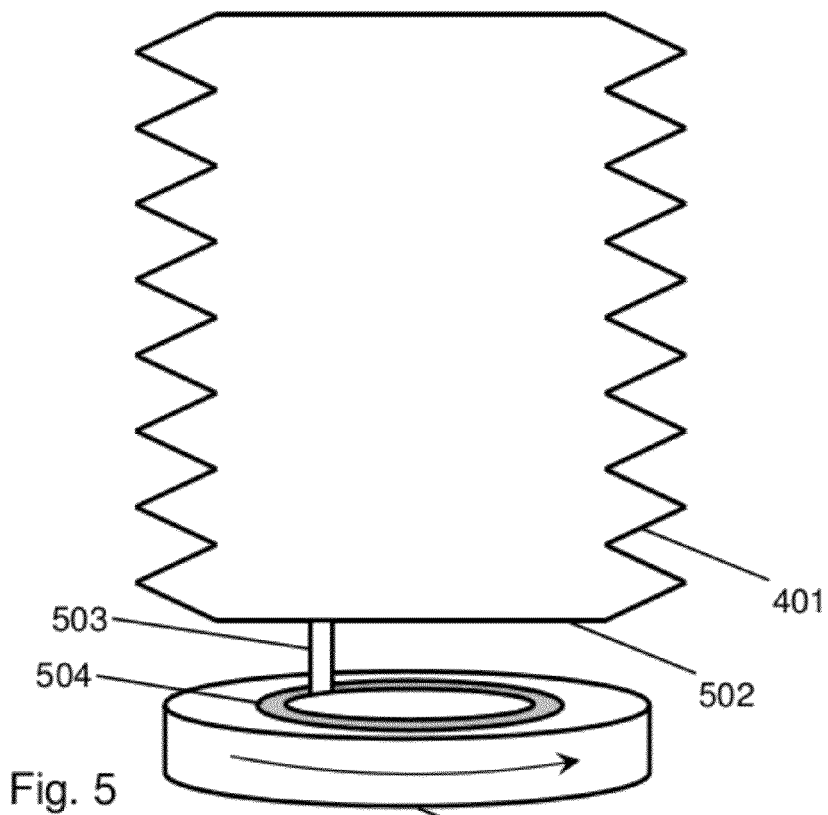
FIG. 5 schematically shows a mover for operating a bellows.

In another embodiment depicted in FIG. 5, a circular plate 501 is located near the moving surface 502 of the bellows 401. One or more pegs 503 extend from the moving surface 502 and contact the plate 501 at a circular groove 504. The depth of the groove 504 varies around its circumference. When the plate 501 rotates, the peg 503 rides up and down in the varying depth of the groove 504 causing the moving surface 502 of the bellows 401 to rise and fall. In this way, the shape of the groove 504, e.g., its depth as a function of its circumference, its radius, etc., can be used to determine the frequency and amount of contraction and expansion of the bellows 401. The plate 501 could include multiple grooves of varying geometry. In this way, a motor could be used to turn the plate 501 at a constant frequency, and the motion of the bellows 401 could be adjusted simply be moving the peg 503 from one groove 504 to another.

A controller 306 is programmed to operate the driver 305, including expanding and contracting the bellows 401 by operating the prime mover 406, and opening and closing the various valves 402, 403, 404 at the appropriate times, depending on the operating state of the driver 305. In some modes, the valves 402, 403, 404 will be arranged so that as the bellows 401 expand, and ambient air 405 is drawn in to charge the device. In a closed mode, the controller 306 will close those valves 402, 403 that connect the interior of the system to the ambient air 405, and operate the device using only the air with which the device is already charged. In general, the controller 306 will cause the driver to pump through multiple consecutive inflation-deflation cycles during the closed mode. The controller 306 may also receive signals from various sensors that may be part of the system, such as an arterial blood pressure sensor, an EKG, a microphone to monitor heart sounds, other types of monitors of cardiac activity, an air pressure sensor detecting the pressure of the air in the system, and/or a humidity sensor detecting moisture in the air in the system. Sensors could be deployed in various places, such as the pump 301, either of the drive lines 302, 304, the arterial interface 307, the skin interface 303, or at locations in the patient's body, not necessarily attached collocated with any part of the device.

When the driver 305 is operating in closed mode, the system will ideally maintain a constant volume of air. The device can include an air pressure sensor that senses the pressure inside the closed system, possibly as a function of time, and transmits a signal representative of that pressure to the controller 306. The controller 306 can be programmed to receive a signal from the pressure sensor and compare the detected pressure to a predetermined normal operating range using a predetermined criterion or criteria. If the criteria are not met, the controller 306 can trigger an error condition. The controller 306 can be programmed to make the comparison using a variety of criteria. For example, the controller 306 could be programmed to trigger the error condition whenever the measured pressure is exceeds or falls below an upper or lower limit. Or the controller 306 could count the instances in which the measured pressure is outside a set range, and trigger the error condition only after a predetermined number of counts have accumulated. For example, the controller could calculate a rolling mean of the detected pressure, and the count could be increased each time the detected pressure is more than two standard deviations different than the mean pressure.

The controller 306 could also measure the amount of time necessary for the balloon pump 301 to inflate once based on the sensed air pressure as a function of time. If the controller detects that the time needed to inflate the balloon pump 301 is shorter or longer than a target time, the controller 306 can lower or raise respectively the amount of power provided to the driver 305 so as to adjust the inflation time to meet the target time. The controller 306 may be programmed to calculate an adjustment to the driver power based on the deviation of the actual inflation time from the target inflation time. The controller 306 may be programmed to include a minimum and maximum power to be input to the driver 305, regardless how the measured inflation time compares to the target inflation time.

The controller 306 can also be programmed to detect air leaks in the system. The constancy of the amount of air in the system can be checked by determining the pressure at a particular time in the pumping cycle, and comparing to the pressure at the same point in previous pumping cycles. If the pressure is the same from cycle to cycle, then the amount of air in the system is not changing. If the pressure has dropped in later cycles, then air must be leaving the system. In this way, an air pressure sensor can be used to detect a leak in the system.

A sensor, such as a humidity sensor, could be connected so as to transmit a signal to the controller 306. The controller 306 could be programmed to receive the signal and determine, based on the signal, whether to operate the driver in closed mode or open mode. In particular, if the sensor is a humidity sensor, the controller 306 could detect that the air in the system has become moist, e.g., during operation in closed mode. The controller 306 could be programmed to switch the driver 305 to open mode in order to exchange moist air in the system with relatively dry ambient air. The controller 306 could be programmed to then switch the driver 305 back to closed mode once the humidity inside the system has achieved an acceptable level.

An EKG sensor could be deployed in the patient so as to detect an EKG signal, which could then be transmitted to the controller 306. The device could also include a pressure sensor that detects or infers a ventricular pressure and is coupled to the controller 306 so as to transmit a signal to the controller 306. The controller 306 could be programmed to use the EKG signal to detect a QRS complex and the pressure signal to detect a dicrotic notch. Various algorithms and methods for QRS detection and dicrotic notch detection are discussed in Hamilton and Tompkins, *Quantitative Investigation of QRS Detection Rules Using the MIT/BIH Arrhythmia Database*, IEEE Transactions on Biomedical Engineering, Vol. BME-33, No. 12, December 1986, Kantrowitz, *Introduction of Left Ventricular Assistance*, ASAIO Journal, Vol. 10, No. 1, January-March 1987, and Pan and Tompkins, *A Real-Time QRS Detection Algorithm*, IEEE Transactions on Biomedical Engineering, Vol. BME-32, No. 3, March 1985, which are incorporated herein by reference. The controller 306 could be programmed to trigger inflation of the pump following the dicrotic notch and deflation of the pump following the QRS complex. The controller 306 could be programmed: first to enter a conservative mode in which the controller 306 detects the QRS complex in order to trigger deflation, but triggers inflation based on other information, for example a guess as to the timing of the dicrotic notch relative to the QRS complex; and second to enter a normal mode in which the controller 306 triggers inflation based on actual detection of the dicrotic notch.

The volume of air needed to achieve the desired pressure inside the balloon pump during diastole can be determined with a searching algorithm. The algorithm can cause the bellows to compress a variety of different amounts during various diastoles, e.g., 75% during a first diastole, 80% during the next diastole, 85% during the next, etc. The pressure in the drive line and/or in the balloon pump can be recorded throughout each of these cycles and analyzed to determine which degree of bellows compression corresponds to a desired pressure increase.

In various embodiments, a ventricular assist device can include an external drive unit with any one of, or any combination of, a variety of features. The drive unit can be a small box designed to be worn externally by a patient. The drive unit can include a rechargeable battery, a transformer, a custom circuit board, custom software, and one or more valve manifolds.

Figure 6:
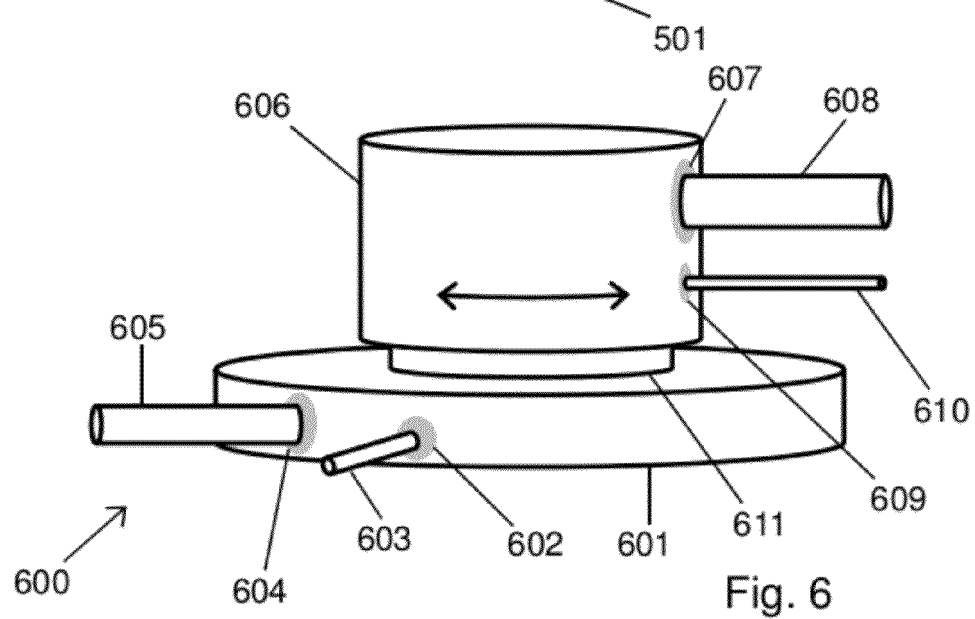
FIG. 6 schematically shows a skin interface.

A skin interface for a ventricular assist device may include a first portion, at least partially internal to, and a second portion external to the patient, that are fixed to one another, but rotatable with respect to one another. One possible embodiment of such a skin interface is shown schematically in FIG. 6. It is possible to implant such a skin interface in a variety of different locations on the patient, for example abdominally or thoracically.

The skin interface 600 has an internal portion 601 that may be implanted in the patient so that at least a part is subcutaneous. The internal portion 601 includes at least one receptacle 602 for receiving one or more internal electrical lines 603 and a receptacle 604 for an internal air line 605. If there are multiple internal electrical lines 603, they may be received in separate receptacles or a single receptacle. The internal electrical line or lines 603 may be connected to one or more sensors. The internal electrical lines 603 can be configured so as to transmit a signal from one or more sensors, such as an arterial blood pressure sensor, an air pressure sensor, or an EKG sensor, to a processor in the skin interface 600. If the skin interface 600 includes a processor, the processor may be programmed to receive signals through the internal electrical lines 603 from the sensors and output the signals. The processor may digitize the signals and produce a digital output indicative of the input received from the sensor or sensors. The skin interface 600 may also include a memory in which patient-specific parameters are stored. The internal air line 605 (or internal drive line) is connected to a balloon pump (not shown) dangling in the patient's aorta.

The skin interface 600 also has an external portion 606. The external portion 606 also includes a receptacle 607 for an external air line 608 and one or more receptacles 609 for one or more external electrical lines 610. The external air line 608 (or external drive line) is connected to an external driver (not shown). The external electrical line 610 may be connected to a processor or a memory in which patient-specific data are stored, both contained in the skin interface 600. The external electrical lines 610 can receive the output from the processor. The external electrical lines 610 may also be connected with the memory so as to allow input to and output from the memory through the external electrical lines 610. The memory could be used to store data accumulated during normal operation of the ventricular assist device, or information obtained during a doctor's visit. The information may be accessed either by a doctor, for example to investigate the past performance of the ventricular assist device or to obtain data on the patient's health as detected by sensors. Or the information may be accessed by a processor in an external driver, for example to set parameters for operation of the ventricular assist device.

The internal and external portions 601, 606 are fixed to one another so that they remain attached to each other but are rotatable with respect to one another. In this way, the internal portion 601 can remain stationary with respect to the patient while the external portion 606 can be rotated to accommodate any convenient orientation of the external air line 608 and external electrical line or lines 610. Such rotational decoupling can help reduce or prevent tugging or other stress on the patient's skin or other organs. The internal and external portions 601, 606 are coupled so as to create an air-tight conduit between the internal and external air line receptacles 604, 607. In this way, the internal and external air lines 605, 608 can be part of a closed fluid system. In one embodiment, an air-tight seal is formed by fixing the internal and external portions 601, 606 to one another using magnets. Gaskets and other sealing systems may be used. The internal and external portions 601, 606 also couple the internal and external electrical line receptacles 602, 609 so as to allow transmission of electrical signals and power through the skin interface 600. Such transmission may be wireless, for example by infrared signals. The skin interface 600 may include a biocompatible surface and/or a finish that promotes biological ingrowth. The internal and external portions 601, 606 may be separated by a medial portion 611.

An intra-aortic balloon pump assembly can include a balloon pump and a drive line with regions of varying cross-sectional area and/or diameter. The size and/or cross-sectional shape of the line is varied to avoid occluding an artery in which part of the line is deployed, while also allowing air to flow effectively through the line. The larger the internal cross-section of the drive line, the easier it is to force air through the drive line. So it is preferable to design a drive line with a large inner diameter or cross-sectional area for as much of its length as possible. On the other hand, where the drive line is deployed within an artery, the line should not be so large as to occlude the artery to the point that the artery cannot provide minimal essential blood flow to downstream tissues. One embodiment of such a balloon pump assembly is shown schematically in FIG. 7.

Figure 7:
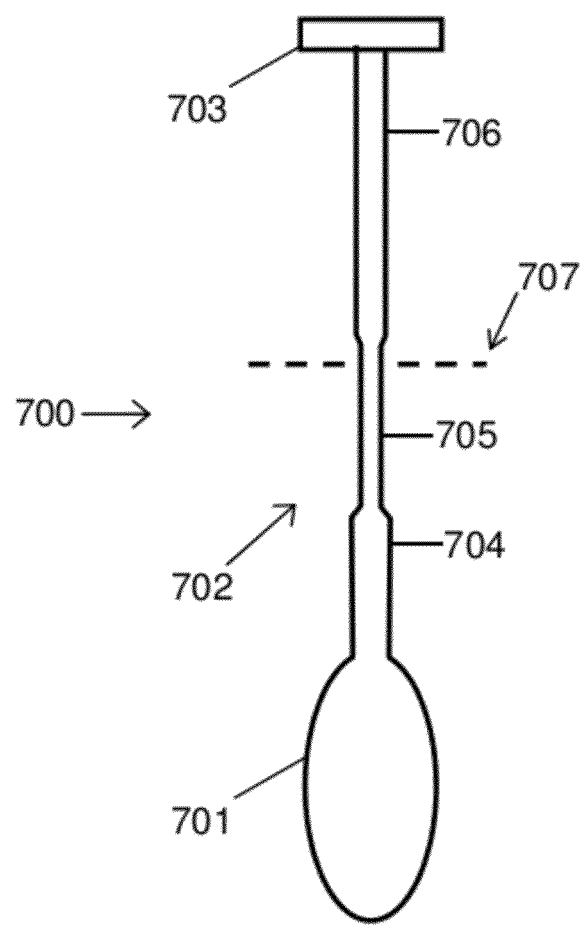
FIGS. 7 and 7A schematically show balloon pump assemblies including a drive line with regions of varying diameter.

The exemplary assembly 700 shown in FIG. 7 includes an intra-aortic balloon pump 701 sized and shaped to dangle inside a patient's aorta, and a drive line 702 with three regions. The drive line 702 forms an air tight connection with the balloon pump 701 at the line's distal end, and connects to a skin interface 703 at the line's proximal end. The drive line 702 has a pump region 704 at its distal end, adjacent to the balloon pump 701. In the middle, the drive line 702 has an arterial region 705. At its proximal end the drive line 702 has an extravascular region 706. The balloon pump 701 may be made at least in part from a moisture-resistant material, such as polyurethane modified with hydrophobic end groups. The hydrophobic end groups could be silicone groups.

The assembly shown in FIG. 7 is designed to be deployed in the body of a patient, extending from a skin interface, through the wall of an artery such as the subclavian artery, into the aorta, where the balloon pump 701 dangles. The drive line 702 can enter the artery through an arterial interface such as those described above. When deployed in the body, the extravascular region 706 extends from the skin interface to near the artery. The arterial region 705 is located generally in the artery and may extend beyond the artery. The pump region 704 is deployed generally in the aorta. The artery wall 707 is schematically represented by the dashed line.

The extravascular region 706 may be designed to have relatively large cross-section to improve air flow. Because the extravascular region 706 of the drive line 702 is not intended to be deployed inside an artery, there is less motivation to minimize the size of the line. The extravascular region 706 may be, for example 4 to 8 mm inner diameter, and in particular 6 mm inner diameter. The pump region 704 may be similarly designed to have a relatively large cross-section, since it is intended to be deployed in the aorta, which is itself large and is unlikely to be occluded by the drive line 702; for example the pump region may have an outer diameter of 6 mm where it meets the pump, so that the pump region 704 is sized and shaped to form an air tight connection with the pump 701. But the arterial region 705 is intended to be deployed in an artery such as the subclavian, and as such it should have an outer diameter sufficiently small to avoid occluding the artery. An arterial region with a cross-sectional area less than 50% of the internal cross-sectional area of the artery is preferred. For the subclavian artery for example, the arterial region 705 could have an outer diameter of about 5 mm. As noted above, the drive line could placed be in any of a variety of arteries, and the geometry of the arterial region would have to be adapted to the particular artery in question. The pump region 704 may be less than 6 cm in length, in particular about 2 to 4 cm, to reach from the orifice of the subclavian artery to where the balloon is intended to rest in the descending aorta. The arterial region 705 could be less than 20 cm in length, in particular about 8 to 15 cm. The extravascular region 706 could be any length necessary to reach from the artery to the skin interface 703, a typical length being about 25 cm. All the dimensions cited above for the various parts of the drive line 702 will depend on the particular anatomy of the patient, the particular artery through which the assembly is deployed, the location of the skin interface, and similar geometrical considerations. The diameters of the pump region 704 and extravascular region 706 could be, but need not be, different from each other. The diameters of the pump region 704 and the extravascular region 706 may be larger than the diameter of the arterial region 705.

Figure 7A:
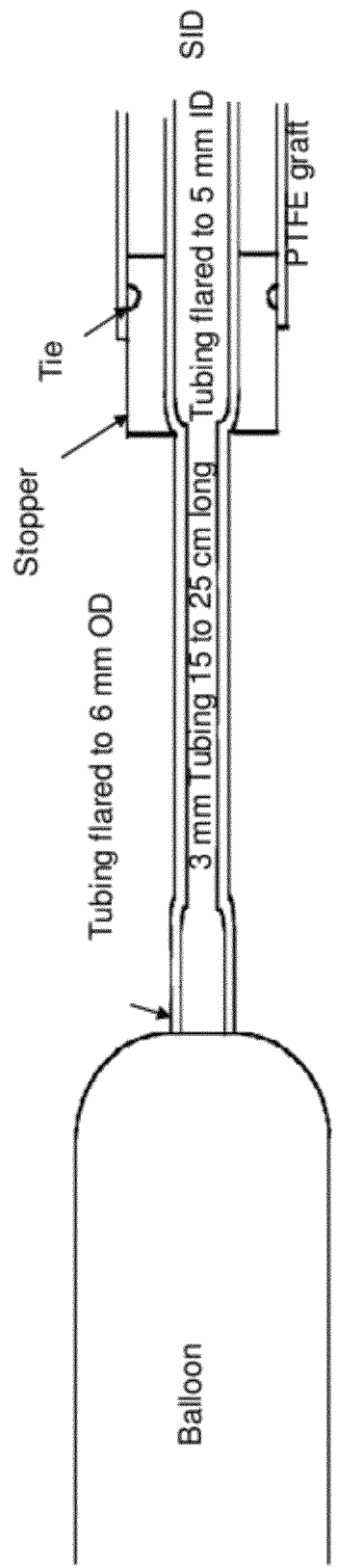

FIG. 7A schematically shows another embodiment of a balloon assembly with a drive line having regions of differing diameter; exemplary dimensions are marked.

In some embodiments, an entire internal drive line and balloon pump may be a single integrally formed piece, and may even include the arterial interface described above. In that case, if and when the balloon pump is replaced, the entire drive line could be replaced down to the skin interface as well. Or the internal drive line could be cut somewhere between the skin interface and the balloon pump, and a new balloon pump and portion of the internal drive line attached to an unreplaced portion of the internal drive line. The old and new portions of the drive line could be attached in any of a variety of ways, for example, adhesives or hose barbs. In other embodiments, the internal drive line may not be integral so that a physician may disconnect parts of the drive line to replace them, leaving other parts of the drive line in place.

Figure 8A:
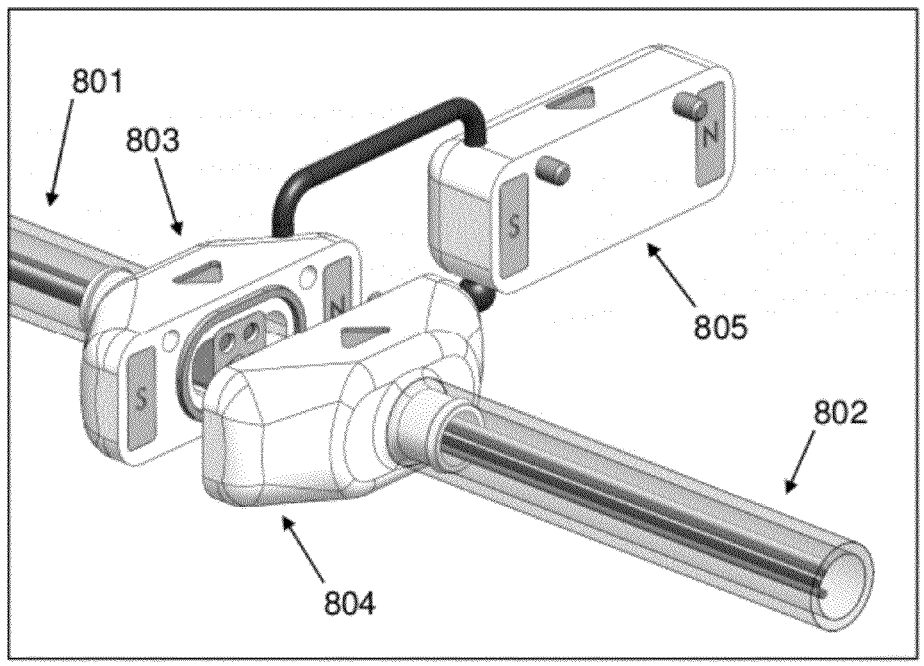
FIGS. 8A and 8B show two views of an embodiment of a patient connector.
Figure 8B:
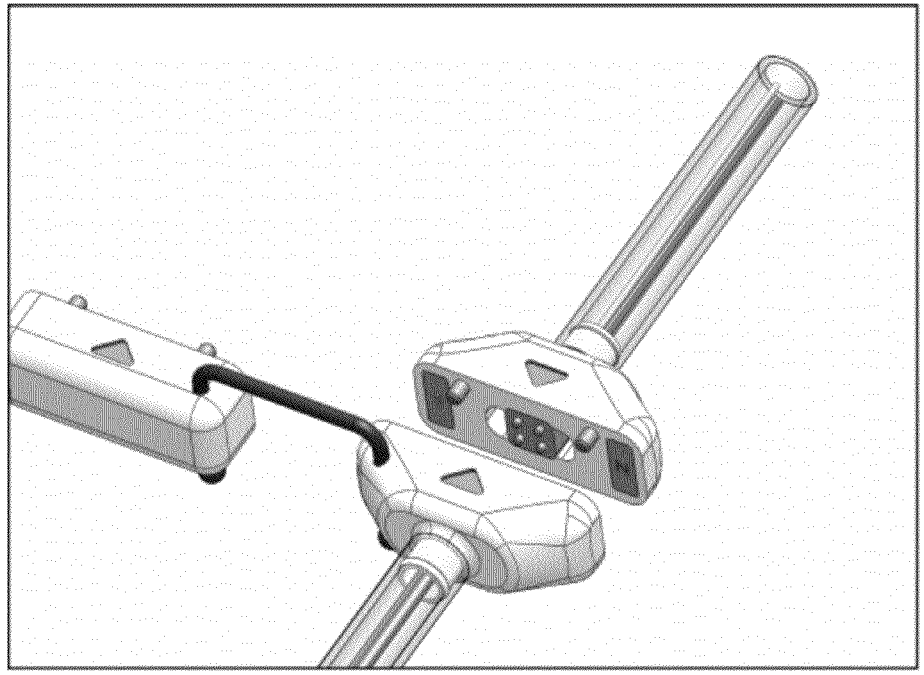

A ventricular assist device can include an external drive line with a detachable patient connector. One possible embodiment of a patient connector is shown in two views in FIGS. 8A & 8B; the figures show the patient connector disconnected for clarity. An external drive line integrated with electrical wires is shown in two parts, a patient-side external drive line 801, and a driver-side external drive line 802. At one end, the patient-side external drive line 801 connects to the patient side of the patient connector 803. At the other end, the patient-side external drive line 801 is connected to the external portion of a skin interface (not shown) implanted in the patient. At one end, the driver-side external drive line 802 connects to the driver side of the patient connector 804. At the other end, the driver-side external drive line 802 is connected to an external driver (not shown). Mating magnets marked "N" and "S" affix the two sides 803, 804 of the patient connector to each other to form an air tight seal. The two sides 803, 804 of the patient connector also form electrical connections for the wires so that signals and power may be transmitted from one side of the connector to the other. By using magnets, the sides of the patient connector are easily attachable and detachable, allowing a patient to disconnect or reconnect the implanted device from an external driver. After disconnecting the two sides 803, 804 of the patient connector, the patient may seal off the patient-side external drive line with a cap, 805, which also includes mating magnets.

As described above, software can be used to control a variety of functions of an external driver in an intraaortic balloon pump system. FIGS. 9-14 describe several such functions. FIGS. 9-14 represent only examples of how software might be used to control such a system, and are not intended to be limiting.

Figure 9:
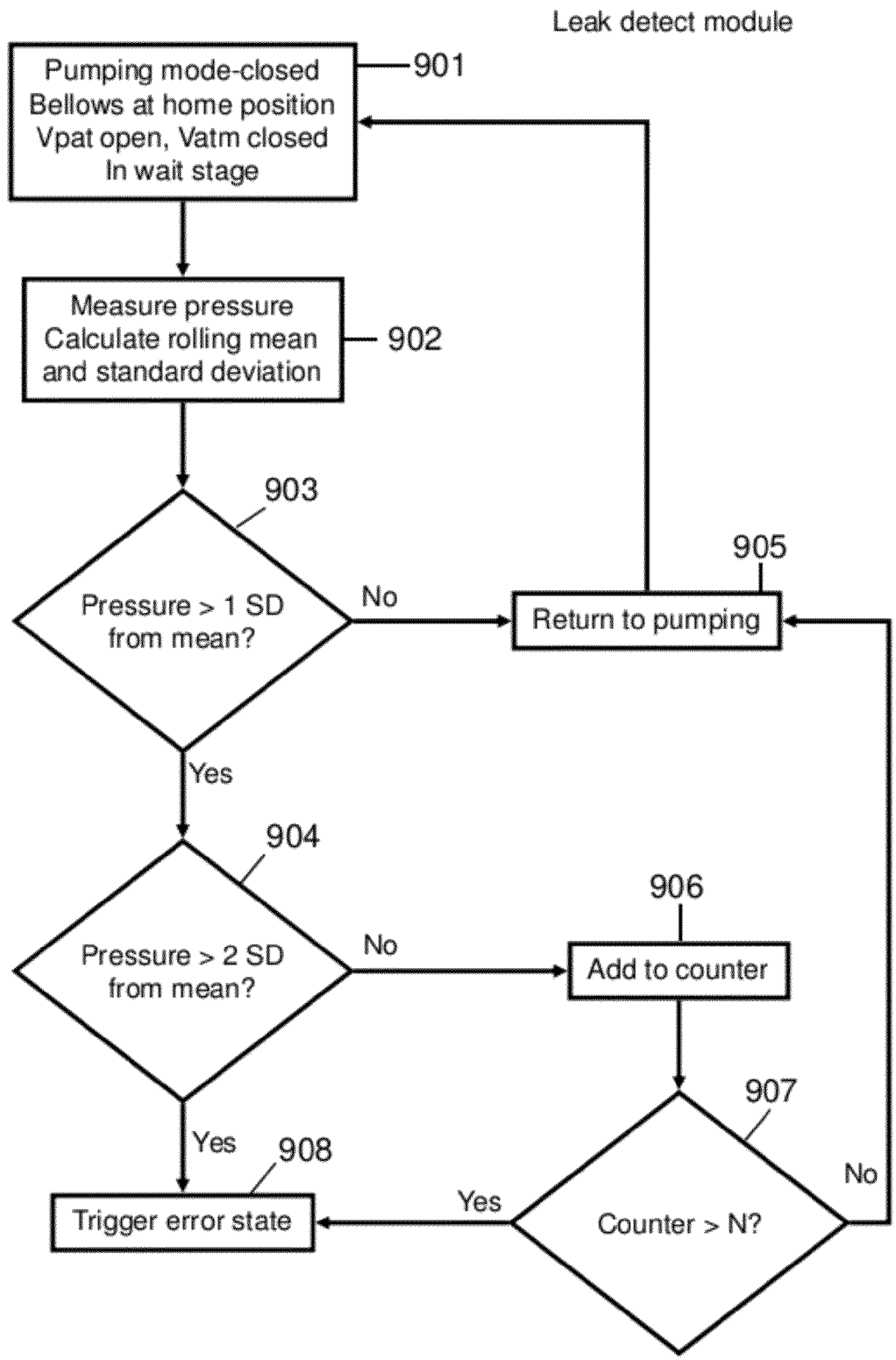
FIG. 9 is a flowchart describing a method of leak detection.

FIG. 9 describes a leak detection function. The system starts by pumping in closed mode 901, and calculates a rolling mean and standard deviation of the measured air pressure inside the balloon pump and/or drive lines at a particular point in each pumping cycle 902. The measured pressure at the chosen point in the pumping cycle is then compared to the mean pressure 903, 904. If the measured pressure is less than one standard deviation away from the rolling mean pressure 903, then the system simply returns to pumping without any further action 905. If the measured pressure is more than one standard deviation away from the rolling mean pressure 903, then the software will ask whether the measured pressure is more than two standard deviations from the rolling mean pressure 904. If not, the system increments an error counter 906. If the error counter has yet to reach a threshold level N 907, then the system returns to normal pumping 905. If the error counter has passed the threshold, then the system triggers an error state 908. Likewise, if the measured pressure is more than two standard deviations from the rolling mean pressure 904, then the system triggers an error state 908.

Figure 10:
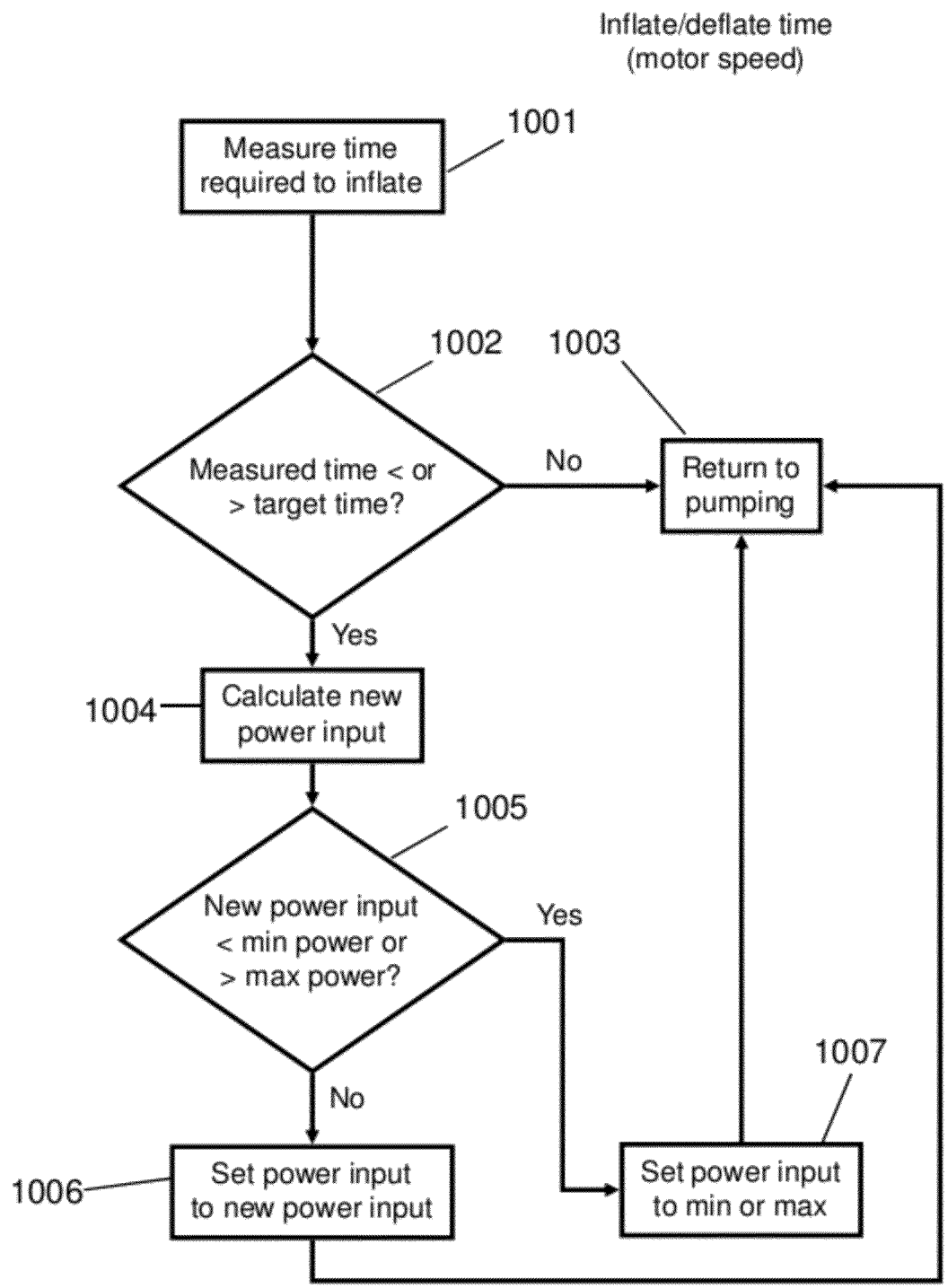
FIG. 10 is a flowchart describing a method of controlling the time needed for inflation of the balloon pump.

FIG. 10 describes a function to adjust the time taken to inflate the balloon pump. The system starts by measuring the time taken to inflate the pump 1001. The system then compares the time to a target time 1002. If the measured time is neither significantly less nor greater than a target time, i.e. the measured time matches a target time, then the system continues to operate with no change in power input to the driver 1003. If the measured time is significantly different than the target time, then the system calculates the power necessary to cause the inflation time to match the target time 1004. If the pump is inflating too slowly, i.e., if the inflation time is significantly greater than the target time, the power supplied to the driver should be increased; if the pump is inflating too quickly, i.e., if the inflation time is significantly less than the target time, the power supplied to the driver should be reduced. After calculating a new power level, the system compares the new power level to the minimum and maximum allowable power levels for the driver 1005. If the new calculated power level is between the minimum and maximum allowable power levels for the driver, the system sets the input power level to the calculated level 1006 and returns to pumping 1003. If the new calculated power level is less than the minimum or greater than the maximum allowable power levels, the system sets the power level to the minimum or maximum respectively 1007 and returns to pumping 1003.

Figure 11:
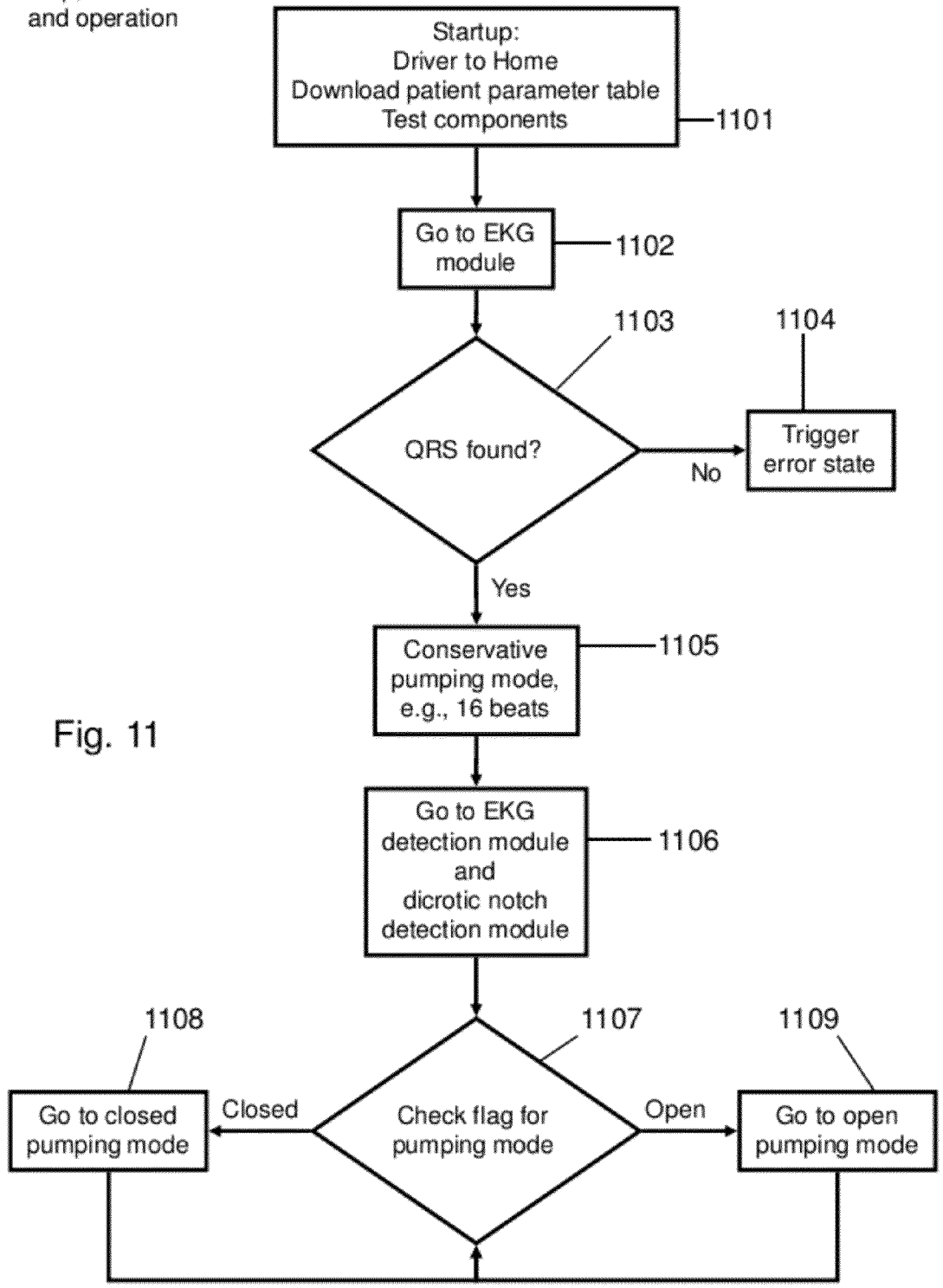
FIG. 11 is a flowchart describing a method of initializing the system.

FIG. 11 describes a method of initializing and starting up the system. On powering up the system, the driver and its actuator are sent to a home position, a patient parameter table is downloaded if available, and tests are run on system components that could include a watchdog timer, memory including non-volatile memory, non-volatile static RAM, ROM, a temperature sensor, pressure transducers, and a battery 1101. At this time, the system may also pressurize to check for leaks. Then an EKG detection module is initiated 1102, which is described in more detail below. If the QRS complex is not successfully detected 1103 by the EKG detection module, then an error state is triggered 1104. If the QRS complex is successfully detected, then a conservative pumping mode is activated for a limited time, say 16 beats 1105. In conservative mode, inflation and deflation are triggered based on a mean "RR interval" (the time between subsequent R-wave peaks) and an expected delay between the R-wave peak and the dicrotic notch; the dicrotic notch is not directly detected. After starting in conservative mode, the system then moves to detect both the QRS complex and the dicrotic notch 1106 to trigger deflation and inflation respectively. Once the QRS complex and dicrotic notch have been successfully detected, the system checks a flag 1107 to see which pumping mode, open or closed, is desired. The system then enters the appropriate mode 1108, 1109 and cycles back to check the flag again 1107 in the next pumping cycle. Open and closed modes 1108, 1109 are described in more detail below.

Figure 12:
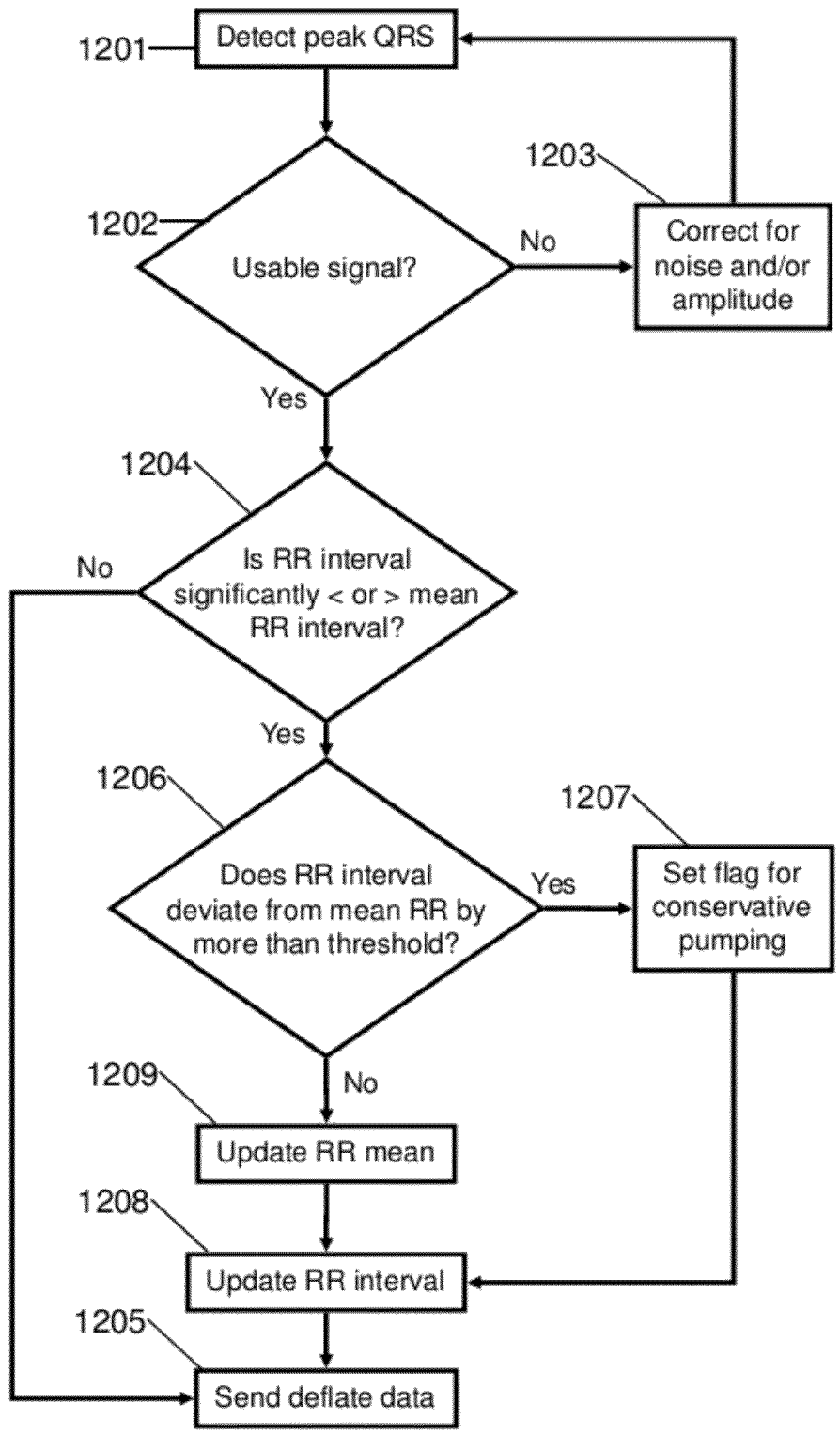
FIG. 12 is a flowchart describing a method of using an EKG signal to detect the QRS complex.

FIG. 12 describes a method of using an EKG signal to time the QRS complex. First the system detects the peak signal of the QRS complex 1201, the R-wave. One example R-wave detection scheme could work as follows. EKG signal peaks will be classified as potential R-wave peaks if (1) the amplitude of the signal exceeds 50% of average signal value and (2) if the slope of the signal exceeds 25% of the average maximum point to point value within a segment. Potential R-wave peaks could be rejected if they occur within 250 milliseconds of a previous R-wave. To reject erroneous T-wave triggers, the slope threshold above could be increased to 50% during the 400 milliseconds following a previous R-wave. Any potential R-waves not rejected in this way could be considered detections of the R-wave. If the signal is of poor quality 1202 the system can correct for noise 1203 and restart the QRS detection 1201. If the signal is usable and an R wave is detected, the system will calculate the current RR interval and compare it to the mean RR interval 1204. If the current RR interval is not significantly different than the mean, the system sends a signal to deflate the balloon pump 1205. If the current RR interval is significantly less than or greater than the mean, then the system checks whether the current RR interval deviates from the mean by more than a predetermined threshold amount 1206. If so, the system goes into conservative pumping mode 1207 subtracting a programmed time interval from the calculated time to deflate. The system updates the previously calculated mean RR interval 1208 and sends the deflation signal 1205. If the current RR interval deviates from the mean by less than a predetermined threshold amount 1206, then the current RR interval is used to update the running mean RR interval 1209, the stored, latest RR interval is updated 1208 and the deflation signal is sent 1205. The system may also use the measured RR interval and its change over time to detect arrhythmia. The system may also detect pulses from a pacemaker and blank those false signals out from the QRS detection scheme.

Figure 13:
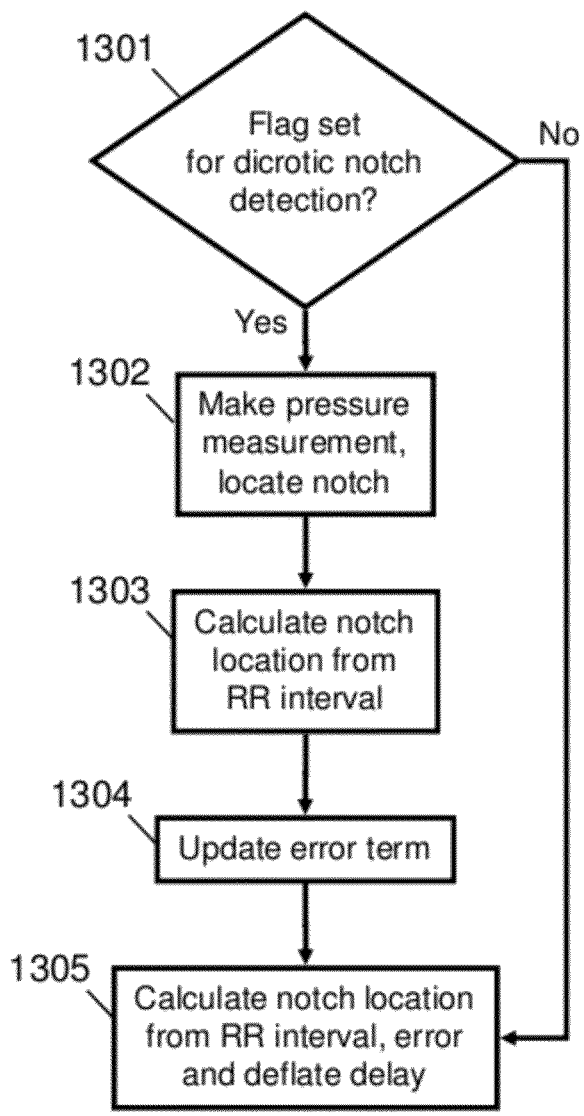
FIG. 13 is a flowchart describing a method of detecting a dicrotic notch.

FIG. 13 describes a method of detecting a dicrotic notch. First, the system will check to see whether a flag is set to indicate whether dicrotic notch detection is indicated 1301. If so, the system makes a pressure measurement to time the dicrotic notch 1302. The dicrotic notch could be detected directly, for instance by a pressure transducer in the aorta, or indirectly, for example by measuring the effect of the ambient arterial blood pressure on the air in the balloon pump. Regardless of the sensor arrangement, multiple criteria are used to determine the dicrotic notch timing, with a statistical weight for each criterion. The primary criterion will be a positive slope in the pressure as a function of time, or if no positive slope is detected, the least negative slope. Notch detection can be improved by only looking for the notch in an appropriate time window. One estimate of the length of time from R-wave peak to dicrotic notch can be calculated as the QS2 interval (based on a second order polynomial); a useful window for dicrotic notch searching would be centered at the end of the calculated QS2, and extend plus or minus some fraction of QS2, for example 25%. When the dicrotic notch is located 1302, the distance of the notch from the R-wave peak is also calculated 1303. The error, i.e. the difference between the QS2-predicted-timing of the dicrotic notch and the actual timing of the dicrotic notch, is also calculated 1304. Based on the distance of the dicrotic notch from the R-wave and the error term, an updated QS2 is then calculated 1305 to be used to estimate the location of the dicrotic notch in the subsequent beat. Constantly updating the QS2 interval and the error term can allow the system to better follow rapidly changing heart rates. Also, if dicrotic notch detection failed entirely, the calculated QS2 plus a previous error term would provide a backup estimate of the timing of the dicrotic notch.

Figure 14:
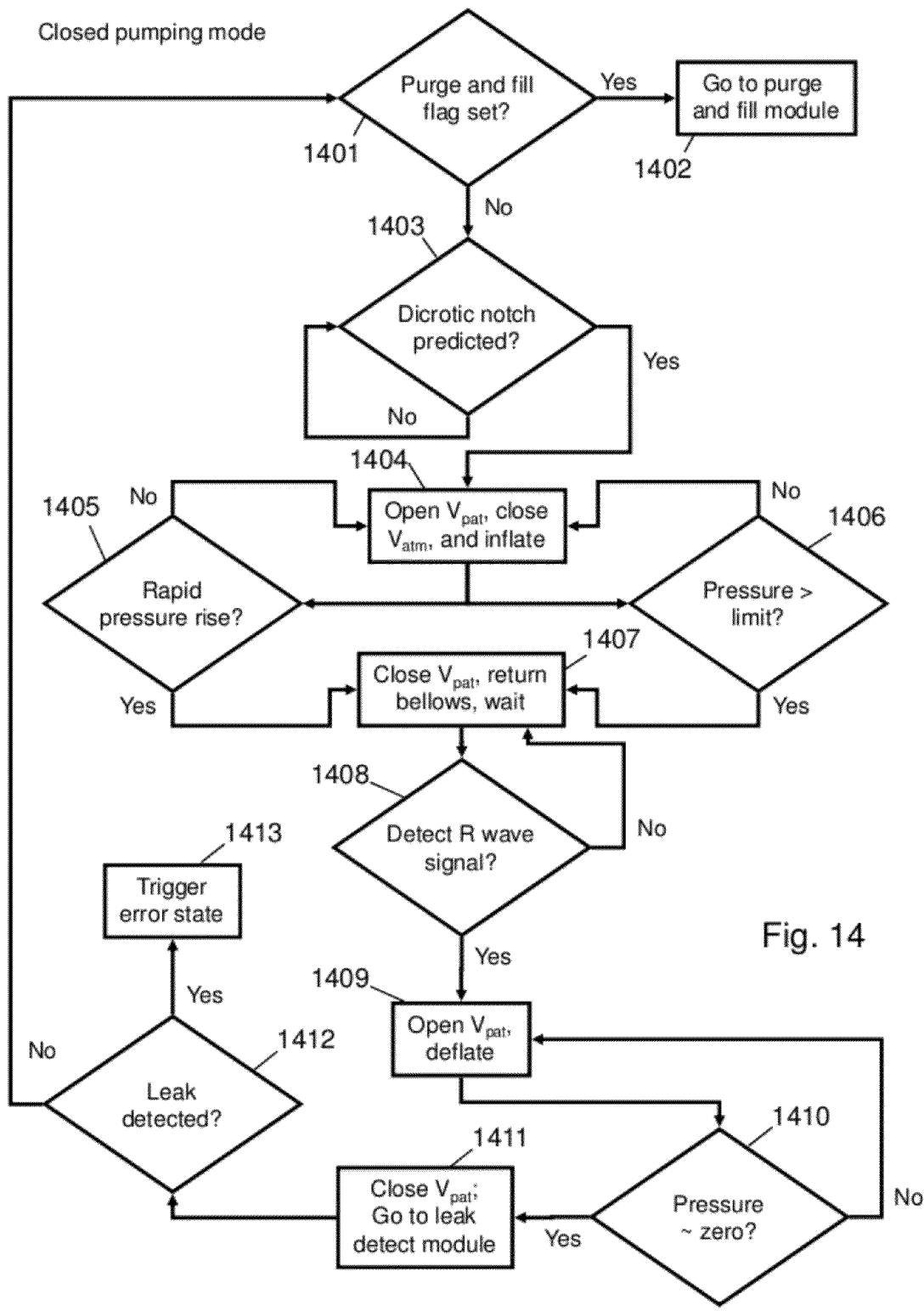
FIG. 14 is a flowchart describing a method of operating the system in closed mode.

FIG. 14 describes how the system can run in a closed pumping mode. First the system checks whether a purge-and-fill flag is set 1401. If so, then the system enters a purge-and-fill mode 1402 described in detail below. If not, the system continues into normal closed pumping mode. If the system has not predicted dicrotic notch 1403, then the system continues to wait; when a dicrotic notch has been predicted, the system proceeds to open $V_{pat}$ (one or more patient-facing valves, e.g., the pump valve 404 of FIG. 4), close $V_{atm}$ (one or more valves open to ambient air, e.g., bellows valve 402 and ambient air valve 403 of FIG. 4), and begins inflating the balloon 1404. The system then checks two conditions, rapid pressure rise 1405, and a pressure limit 1406. If the pressure rise is not overly rapid 1405, and if the pressure does not reach a limit value 1406, then the system continues inflation 1404. If either condition 1405, 1406 is met then the system closes $V_{pat}$ and returns the bellows to a neutral position 1407. With the balloon pump inflated, the system then checks whether an R-wave is detected 1408. If no R-wave is detected the system continues to wait 1407. If an R-wave is detected, the system opens $V_{pat}$ and begins deflating the balloon pump 1409. The system then checks whether the air pressure in the system has reached roughly zero, i.e. whether the air pressure in the balloon pump has equilibrated with the surrounding blood pressure 1410. If not, the system continues to deflate the balloon pump 1409; if so, the system closes $V_{pat}$ and proceeds to the leak detection module described above 1411. If a leak is detected 1412, then the system triggers an error state 1413. If no leak is detected, the system returns to the beginning of the cycle to check whether the purge and fill flag has been set 1401. This process is further explained in Table 1:

TABLE 1

| Stage | Event | Start | End | $V_{pat}$ | $V_{atm}$ | Bellows and actuator |
|---|---|---|---|---|---|---|
| 1 | Deflation | R-wave plus deflation delay | Bellows in home position (pressure reaches roughly zero) | Open | Closed | Return to home, deflate |
| 2 | Wait | Bellows reach home position | Dicrotic notch plus inflation delay | Open | Closed | Wait |
| 3 | Leak Detection | As soon as stage 2 begins | When leak detection module finishes | Closed | Closed | Wait |
| 4 | Inflation | Dicrotic notch plus inflation delay | Rapid rise in pressure or pressure past limit | Open | Closed | Actuate, compress and inflate |
| 5 | Wait | Rapid rise in pressure or pressure past limit | R-wave plus deflation delay | Closed | Closed | Wait |

Figure 15:
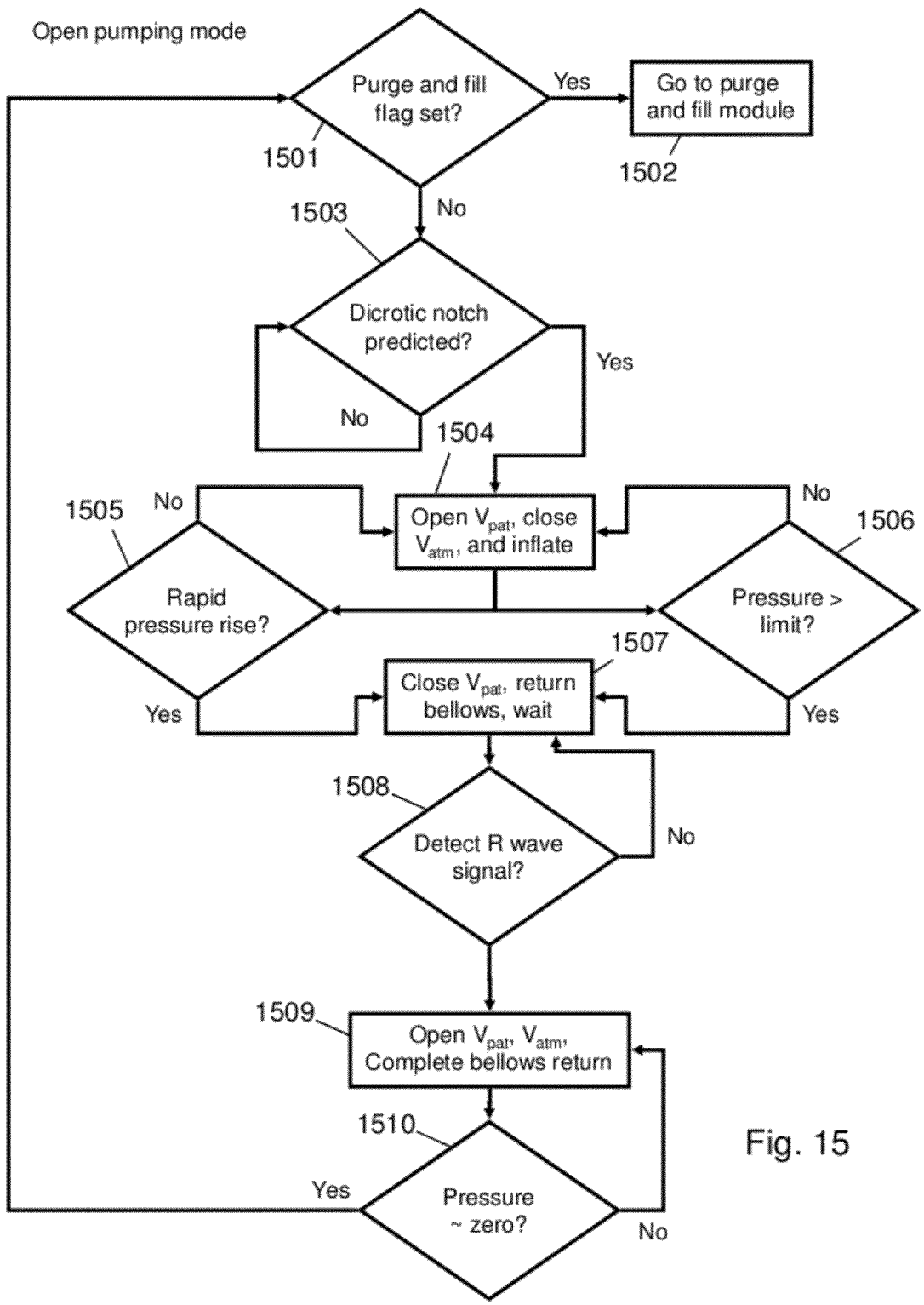
FIG. 15 is a flowchart describing a method of operating the system in open mode.

FIG. 15 describes how the system can run in a open pumping mode. First the system checks whether a purge-and-fill flag is set 1501. If so, then the system enters a purge-and-fill mode 1502 described in detail below. If not, the system continues into normal open pumping mode. If the system has not predicted dicrotic notch 1503, then the system continues to wait; when a dicrotic notch has been predicted, the system proceeds to open $V_{pat}$, close $V_{atm}$, and begins inflating the balloon 1504. The system then checks two conditions, rapid pressure rise 1505, and a pressure limit 1506. If the pressure rise is not overly rapid 1505, and if the pressure does not reach a limit value 1506, then the system continues inflation 1504. If either condition 1505, 1506 is met then the system closes $V_{pat}$ and returns the bellows to a neutral position 1507. With the balloon pump inflated, the system then checks whether an R-wave is detected 1508. If no R-wave is detected the system continues to wait 1507. If an R-wave is detected, the system opens $V_{pat}$ and $V_{atm}$, and returns the bellows to the home position 1509. By opening $V_{atm}$, the balloon is allowed to deflate, exhausting the air with which it was inflated 1504. At the same time, because the compressed bellows are decompressed with $V_{atm}$ open, the bellows draw in fresh ambient air. The system then checks whether the air pressure in the system has reached roughly zero, i.e. whether the air pressure in the balloon pump has equilibrated with the surrounding blood pressure 1510. If not, the system continues to allow the balloon pump to deflate while the bellows draw in fresh air 1509; if so, the system returns to the beginning of the cycle to check whether the purge and fill flag has been set 1501. This process is further explained in Table 2.

TABLE 2

| Stage | Event | Start | End | $V_{pat}$ | $V_{atm}$ | Bellows and actuator |
|---|---|---|---|---|---|---|
| 1 | Deflation | R-wave plus deflation delay | Bellows in home position (pressure reaches roughly zero) | Open | Open | Return to home, deflate |
| 2 | Wait | Bellows reach home position | Dicrotic notch plus inflation delay | Open | Open | Wait |
| 3 | Inflation | Dicrotic notch plus inflation delay | Rapid rise in pressure or pressure past limit | Open/Closed* | Closed | Actuate, compress and inflate |
| 4 | Wait | Rapid rise in pressure or pressure past limit | R-wave plus deflation delay | Open/Closed* | Closed | Wait |

Figure 16:
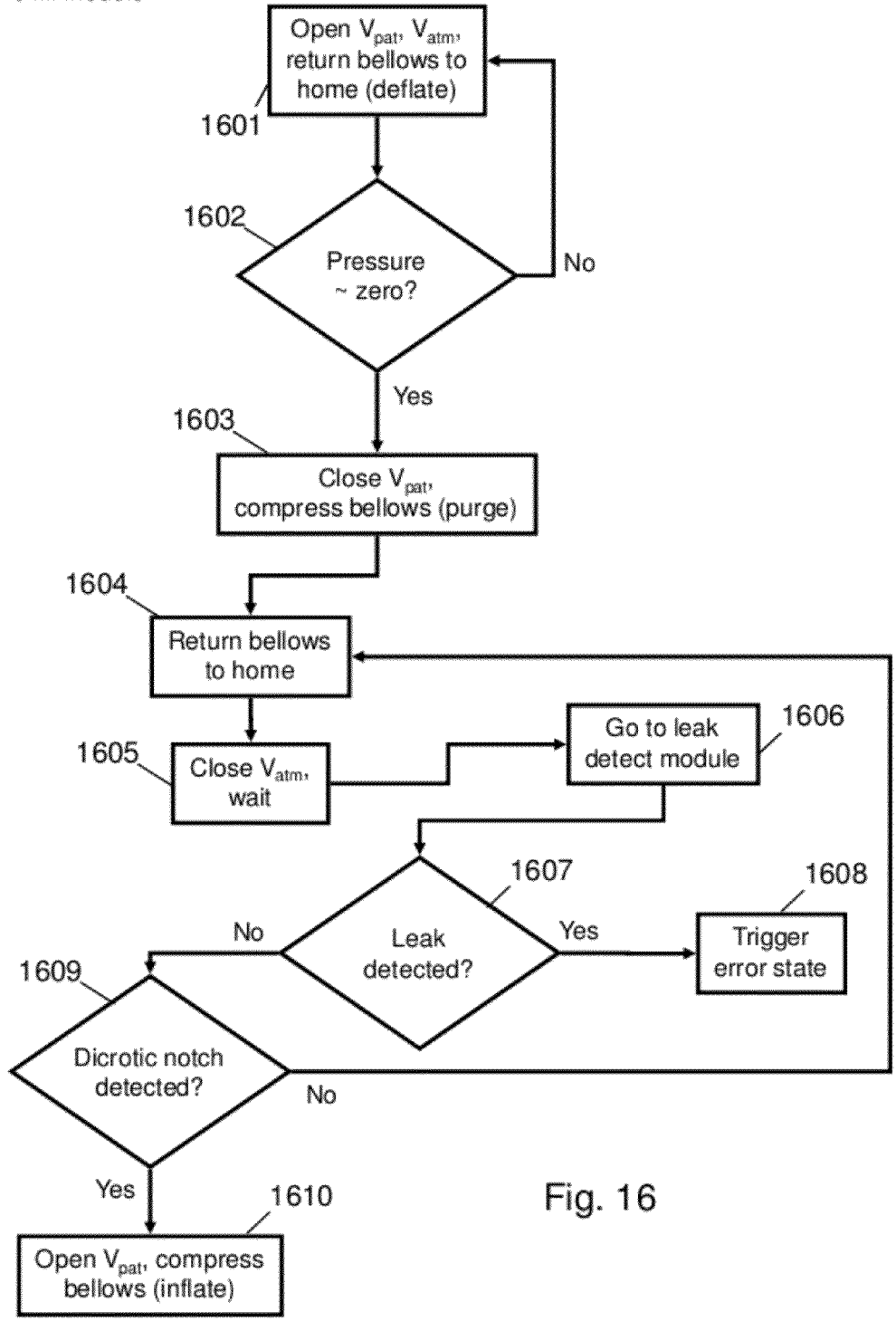
FIG. 16 is a flowchart describing a method of purging and filling the system with ambient air.

*If there are multiple $V_{pat}$ valves, they may be closed during the first wait and then opened in pairs with a predetermined delay, e.g., 20 milliseconds, between openings. This may be discontinued at higher heart rates or when the actuator motor is operating at maximum speed FIG. 16 describes a method of purging air from the system and replacing it with ambient air. First the system opens both $V_{pat}$ and $V_{atm}$, and returns the bellows to the home position in order to fully deflate the balloon pump 1601. If the pressure in the system has not reached roughly zero 1602, then the system continues to expand the bellows and leave the valves open. When the pressure has reached roughly zero, the system closes $V_{pat}$ and compresses the bellows with $V_{atm}$ still open, so as to purge the air from the bellows 1603. No air is sent to the balloon pump at this time because $V_{pat}$ is closed. The bellows are then returned to home position, again drawing fresh air into the bellows 1604. Once the bellows have been filled with ambient air, the system closes $V_{atm}$ 1605 and enters the leak detection module 1606. If a leak is detected 1607, the system triggers an error state 1608; otherwise the system checks whether a dicrotic notch has been detected or predicted 1609. If not, the system again returns the bellows to home 1604 and waits for a dicrotic notch detection. If a dicrotic notch is detected 1609, then the system opens $V_{pat}$ and compresses the bellows with $V_{atm}$ still closed 1610, driving the fresh ambient air from the bellows into the balloon pump. From this state, the system could enter normal closed pumping mode. Table 3 further describes how a purge/fill module could be implemented.

We claim:

1. An intra-aortic balloon pump assembly comprising:
an intra-aortic balloon pump sized and shaped to dangle inside a patient's aorta, the pump having a wall made at least in part from a moisture-resistant material; and
an internal drive line with a first end adapted to be connected to a skin interface device and a second end forming an air tight connection to the balloon pump;
an arterial interface, sized and shaped to pass the drive line through an arterial wall, the arterial interface comprising a vascular graft and a stopper;
wherein:
the internal drive line has an extravascular region adjacent to the first end, a pump region adjacent to the second end, and an arterial region between the extravascular region and the pump region;
the cross-sectional area of the arterial region is less than 50% of the internal cross-sectional area of the artery in which it is to be deployed;
the cross-sectional areas of the extravascular and pump regions are larger than the cross-sectional area of the arterial region;

TABLE 3

| Stage | Event | Start | End | $V_{pat}$ | $V_{atm}$ | Bellows and actuator |
|---|---|---|---|---|---|---|
| 1 | Deflation | R-wave plus deflation delay | Bellows in home position | Open | Closed | Return to home, deflate |
| 2 | Purge | Bellows reach home position | Pressure reaches roughly zero | Closed | Open | Compressing |
| 3 | Fill | Dicrotic notch plus inflation delay | Bellows in home position | Closed | Open | Return to home |
| 4 | Wait | Bellows reach home position | Dicrotic notch plus inflation delay | Open | Closed | Wait |
| 5 | Leak Detection | As soon as stage 4 begins | When leak detection module finishes | Closed | Closed | Wait |
| 6 | Inflation | Dicrotic notch plus inflation delay | Rapid rise in pressure or pressure past limit | Open | Closed | Actuate, compress and inflate |

19 the diameter of the pump region is sized and shaped to connect to the pump;
the vascular graft defines a graft lumen and comprises a distal end so sized and shaped as to be suited for grafting to an artery;
the stopper is secured to and immobilized relative to the graft and fills the graft lumen except for a hole defined through the stopper's length, the hole providing a conduit through the graft lumen;
the internal drive line passes through the conduit;
the graft lumen is wide enough to allow passage of the balloon pump; and
the conduit is too narrow to allow passage of the balloon pump.

2. The assembly of claim 1, wherein:
the extravascular region has an inner diameter of 4 to 8 mm;
the arterial region has an outer diameter of about 5 mm and is adapted to be deployed in the subclavian artery; and
the pump region has an outer diameter of about 6 mm.

3. The assembly of claim 1, wherein the balloon pump comprises polyurethane modified with hydrophobic end groups.

4. The assembly of claim 3, wherein the hydrophobic end groups are silicone groups.

5. The assembly of claim 3, further comprising an arterial interface, sized and shaped to pass the drive line through an arterial wall, the arterial interface comprising a vascular graft and a stopper;
wherein:
the vascular graft defines a graft lumen and comprises a distal end so sized and shaped as to be suited for grafting to an artery;
the stopper is secured to and immobilized relative to the graft and fills the
graft lumen except for a hole defined through the stopper's length, the hole providing a conduit through the graft lumen;
the internal drive line passes through the conduit and is immobilized relative to the stopper;
the graft lumen is wide enough to allow passage of the balloon pump; and the conduit is too narrow to allow passage of the balloon pump.

6. A ventricular assist device comprising the intra-aortic balloon pump assembly of claim 1 and further comprising:
a skin interface;
an external driver comprising a rigid bellows, a prime mover actuating the bellows, and valves arranged to permit multiple pumping modes, the prime mover being operably connected to a power source;
an arterial interface, sized and shaped to pass the internal drive line through an arterial wall;
an external drive line connecting the skin interface to the external driver; and a controller;
wherein:
the balloon pump, the internal drive line, the skin interface, the external drive line, and the driver form a fluid system for containing pumping air to act as a pumping medium; and
the controller is programmed to:
operate the valves and the prime mover such that the pumping air is not pressurized more than a predetermined amount above a sensed blood pressure;
cause the valves to adopt a closed pumping mode in which no air is added to or vented from the fluid system;
cause the external driver to pump through multiple consecutive inflation-deflation cycles during the closed mode;

20 cause the valves to adopt an open mode in which contraction of the bellows by the prime mover causes air in the fluid system to be vented from the fluid system and expansion of the bellows by the prime mover causes ambient air to be drawn into the fluid system, thereby charging the fluid system with new pumping air to act as the pumping medium.

7. The device of claim 6, wherein the predetermined amount is 40 mmHg.

8. The device of claim 6, further comprising an air pressure sensor configured to detect the pumping air pressure inside the fluid system, the air pressure sensor being so connected to the controller as to allow transmission of a signal representative of the pumping air pressure to the controller, and wherein the controller is programmed to
receive the signal from the air pressure sensor;
compare the pressure of the air column to a predetermined normal operating range by a predetermined set of operating criteria; and
trigger an error state if the pressure is outside the normal operating range.

9. The device of claim 8, wherein
operating the prime mover includes controlling the amount of power provided to the prime mover from the power source;
the air pressure sensor is configured to detect the air pressure inside the closed fluid system as a function of time; and
the controller is further programmed to:
based on the signal from the air pressure sensor, determine the time taken to inflate the balloon pump once;
compare the time required to inflate the balloon pump to a target time stored in the controller;
if the time required to inflate the balloon is not within a predetermined range of the target time, calculate the power input to the external driver necessary to cause the time required to inflate the balloon to match the target time; and
adjust the amount of power subsequently provided to the driver based on the calculation.

10. The device of claim 6, further comprising a humidity sensor connected to the
controller so as to allow transmission of a signal to the controller, the signal representative of a humidity of the pumping air in the fluid system detected by the sensor; and
wherein the controller is programmed to determine based on the signal from the humidity sensor whether to operate the driver in the closed mode or the open mode.

11. The device of claim 6, further comprising an electrocardiogram sensor and a pressure sensor;
wherein the electrocardiogram sensor detects an electrocardiogram signal, and is so coupled to the controller as to allow transmission of an electrocardiogram signal to the controller;
wherein the pressure sensor detects or infers a ventricular pressure and is so coupled to the controller as to allow transmission of a pressure signal to the controller; and
wherein the controller is programmed to
detect a QRS complex based on the electrocardiogram signal;
detect a dicrotic notch based on the pressure signal;
trigger the driver to deflate the pump following the QRS complex and inflate the pump following the dicrotic notch.

12. The device of claim 6, wherein the skin interface comprises:
- two portions fixed to one another and rotatable with respect to one another;
- receptacles for receiving air and electrical lines on both portions;
- an air-tight conduit between the receptacles and running through the interface, for transmitting air through the interface;
- a wireless electrical coupling between the receptacles, for transmitting electrical signals and power through the interface;
- a memory in which patient-specific parameters are stored; and
- a processor configured to receive the electrical signals, digitize them, and produce a digital output indicative of the electrical signals;
- wherein the processor and the memory are in communication with the wireless electrical coupling.

13. The device of claim 6, wherein the controller is configured to receive (a) a blood pressure signal representative of at least a sensed blood pressure, and (b) an electrocardiogram signal, and the controller is programmed to detect a QRS complex based on an electrocardiogram signal received by the controller; detect a dicrotic notch based on a blood pressure signal received by the controller; and trigger the driver to deflate the pump following the QRS complex and inflate the pump following the dicrotic notch.

* * * * *